US009663432B2

(12) United States Patent
Souda et al.

(10) Patent No.: US 9,663,432 B2
(45) Date of Patent: May 30, 2017

(54) HIGH-PURITY MONOALKENYL-CONTAINING GLYCERIN DERIVATIVE AND METHOD OF MANUFACTURING SAME

(71) Applicant: Dow Corning Toray Co., Ltd., Tokyo (JP)

(72) Inventors: Tatsuo Souda, Ichihara (JP); Sayuri Sawayama, Ichihara (JP); Tsunehito Sugiura, Ichihara (JP); Seiki Tamura, Ichihara (JP); Seiji Hori, Sabae (JP)

(73) Assignee: DOW CORNING TORAY CO., LTD., Tokyo (JP)

( * ) Notice: Subject to any disclaimer, the term of this patent is extended or adjusted under 35 U.S.C. 154(b) by 0 days.

(21) Appl. No.: 14/655,166

(22) PCT Filed: Dec. 26, 2013

(86) PCT No.: PCT/JP2013/085004
§ 371 (c)(1),
(2) Date: Oct. 9, 2015

(87) PCT Pub. No.: WO2014/104255
PCT Pub. Date: Jul. 3, 2014

(65) Prior Publication Data
US 2016/0052849 A1    Feb. 25, 2016

(30) Foreign Application Priority Data
Dec. 28, 2012  (JP) .................................. 2012-289018

(51) Int. Cl.
| | | |
|---|---|---|
| C07C 43/178 | (2006.01) | |
| A61K 8/893 | (2006.01) | |
| C07C 41/03 | (2006.01) | |
| C07C 41/28 | (2006.01) | |
| A61Q 19/00 | (2006.01) | |
| C08G 77/38 | (2006.01) | |
| C08G 77/14 | (2006.01) | |
| A61K 8/895 | (2006.01) | |
| A61Q 1/02 | (2006.01) | |
| A61Q 17/04 | (2006.01) | |
| C07C 41/18 | (2006.01) | |

(52) U.S. Cl.
CPC .......... *C07C 43/1785* (2013.01); *A61K 8/893* (2013.01); *A61K 8/895* (2013.01); *A61Q 1/02* (2013.01); *A61Q 17/04* (2013.01); *A61Q 19/00* (2013.01); *C07C 41/03* (2013.01); *C07C 41/18* (2013.01); *C07C 41/28* (2013.01); *C08G 77/14* (2013.01); *C08G 77/38* (2013.01); *A61K 2800/10* (2013.01)

(58) Field of Classification Search
CPC ........ C07C 33/025; C07C 41/03; C07C 29/36
See application file for complete search history.

(56) References Cited

U.S. PATENT DOCUMENTS

| | | | | |
|---|---|---|---|---|
| 4,465,866 A * | 8/1984 | Takaishi | ................ | C07C 43/135 549/453 |
| 4,683,347 A * | 7/1987 | Diaz | ...................... | C07C 29/86 568/859 |
| 5,135,683 A * | 8/1992 | Cooper | ................... | C07C 41/28 536/116 |
| 6,211,322 B1 | 4/2001 | Dohler et al. | | |
| 8,715,626 B2 | 5/2014 | Tamura et al. | | |
| 8,784,787 B2 | 7/2014 | Tamura et al. | | |
| 9,133,309 B2 | 9/2015 | Iimura et al. | | |
| 2002/0090383 A1* | 7/2002 | Eibl | ..................... | A61K 9/1271 424/400 |

(Continued)

FOREIGN PATENT DOCUMENTS

| | | |
|---|---|---|
| EP | 0 940 422 A1 | 9/1999 |
| EP | 1 405 669 A2 | 4/2004 |

(Continued)

OTHER PUBLICATIONS

Cassel et al., "Original Synthesis of Linear, Branched and Cyclic Oligoglycerol Standards", Eur. J. Org. Chem. 2001, pp. 875-896.
International Search Report for Application No. PCT/JP2013/085004 dated Apr. 1, 2014, 5 pages.
English language abstract for EP 0 940 422 extracted from espacenet.com database on Oct. 19, 2015, 1 page.
English language abstract and machine-assisted English translation for JPH 09-071504 extracted from the PAJ database on Oct. 19, 2015, 18 pages.

(Continued)

*Primary Examiner* — Marc Zimmer
(74) *Attorney, Agent, or Firm* — Howard & Howard Attorneys PLLC

(57) ABSTRACT

The present invention relates to a monoalkenyl-containing glycerin derivative with purity of not less than 92% and electrical conductivity of not greater than 50 µS/cm. The monoalkenyl-containing glycerin derivative can be manufactured by a manufacturing method comprising a step (A): a step of reacting a ketalized glycerin derivative and a monoalkenyl glycidyl ether in the presence of an inorganic base to obtain a ketal of monoalkenyl-containing glycerin derivative; a step (B): a step of purifying the ketal of monoalkenyl-containing glycerin derivative obtained in the step (A) by distillation; and a step (C): a step of hydrolyzing the ketal of monoalkenyl-containing glycerin derivative obtained in the step (B). The present invention is able to provide a high-purity monoalkenyl-containing glycerin derivative that was difficult in the past. It is further able to provide a glycerin derivative-modified silicone, and applications therefor, that is chemically stable, and further has excellent utility for its emulsifiability, and the like, and excellent formulation stability.

7 Claims, No Drawings

(56) References Cited

U.S. PATENT DOCUMENTS

| | | | |
|---|---|---|---|
| 2004/0077904 A1 | 4/2004 | Nagasawa et al. | |
| 2006/0252946 A1 | 11/2006 | Nagasawa et al. | |
| 2008/0085980 A1* | 4/2008 | Sakanishi | C07C 41/03 526/173 |
| 2010/0222603 A1* | 9/2010 | Selifonov | C07C 43/132 549/448 |
| 2012/0269748 A1 | 10/2012 | Tamura et al. | |
| 2013/0150458 A1 | 6/2013 | Iyoku | |
| 2015/0080480 A1 | 3/2015 | Tamura et al. | |

FOREIGN PATENT DOCUMENTS

| | | | |
|---|---|---|---|
| EP | 2 602 279 A1 | 6/2013 | |
| JP | 58-039680 | * | 3/1983 |
| JP | H 09-071504 A | 3/1997 | |
| JP | H 09-235247 A | 9/1997 | |
| JP | H 10-310505 A | 11/1998 | |
| JP | H 10-316526 A | 12/1998 | |
| JP | H 10-316527 A | 12/1998 | |
| JP | H 10-316536 A | 12/1998 | |
| JP | H 10-316540 A | 12/1998 | |
| JP | H 11-315144 A | 11/1999 | |
| JP | 2004-105959 A | 4/2004 | |
| JP | 2004-277548 A | 10/2004 | |
| JP | 2007-031554 A | 2/2007 | |
| JP | 2012-046507 A | 3/2012 | |
| JP | 2013-119596 A | 6/2013 | |
| JP | 2013-151658 A | 8/2013 | |
| WO | WO 2011/049246 A1 | 4/2011 | |
| WO | WO 2011/049247 A1 | 4/2011 | |
| WO | WO 2011/049248 A1 | 4/2011 | |
| WO | WO 2012/172457 A1 | 12/2012 | |

OTHER PUBLICATIONS

English language abstract and machine-assisted English translation for JPH 09-235247 extracted from espacenet.com database on Oct. 19, 2015, 25 pages.

English language abstract and machine-assisted English translation for JPH 10-310505 extracted from espacenet.com database on Oct. 19, 2015, 14 pages.

English language abstract and machine-assisted English translation for JPH 10-316526 extracted from espacenet.com database on Oct. 19, 2015, 11 pages.

English language abstract and machine-assisted English translation for JPH 10-316527 extracted from espacenet.com database on Oct. 19, 2015, 14 pages.

English language abstract and machine-assisted English translation for JPH 10-316536 extracted from espacenet.com database on Oct. 19, 2015, 15 pages.

English language abstract and machine-assisted English translation for JPH 10-316540 extracted from espacenet.com database on Oct. 19, 2015, 13 pages.

English language abstract for JPH 11-315144 extracted from espacenet.com database on Oct. 19, 2015, 2 pages.

English language abstract for JP 2004-105959 extracted from espacenet.com database on Oct. 19, 2015, 1 page.

English language abstract and machine-assisted English translation for JP 2004-277548 extracted from espacenet.com database on Oct. 19, 2015, 36 pages.

English language abstract and machine-assisted English translation for JP 2007-031554 extracted from espacenet.corn database on Oct. 19, 2015, 23 pages.

English language abstract for JP 2012-046507 extracted from espacenet.com database on Oct. 19, 2015, 1 page.

English language abstract for JP 2013-119596 extracted from espacenet.com database on Oct. 19, 2015, 1 page.

English language abstract not found for JP 2013-151658; however, see English language equivalent U.S. 2015/0080480. Original document extracted from espacenet.com database on Oct. 19, 2015, 64 pages.

English language abstract for WO 2011/049246 extracted from espacenet.com database on Oct. 19, 2015, 2 pages.

English language abstract for WO 2011/049247 extracted from espacenet.com database on Oct. 19, 2015, 2 pages.

English language abstract for WO 2011/049248 extracted from espacenet.com database on Oct. 19, 2015, 2 pages.

Foulard, G. et al., "Sequential Radical Perfluoroalkylation-Nucleophilic Cyclization, Synthesis of 2-Perfluoralkylidenemethyl and 2-Perfluoroalkylmethyl-1,4-dioxanes from 1-0-allyl-1,2-diols", Tetrahendron, Elsevier Science Publishers, Amsterdam, NL, vol. 52, No. 17, Apr. 22, 1996, pp. 6187-6200, XP004104179, ISSN: 0040-4020, DOI: 10.1016/0040-4020(96)00243-8.

Hamada, M. et al., "Short and Stereocontrolled Cyclic Polyglycerols Synthesis Using BF3-OEI2 Mediated Intramolecular Epoxide-Opening Reaction", Heterocycles Communication: Special Issue, vol. 86, Aug. 17, 2012, pp. 1533-1539.

Moghadam, M. et al., "Rapid and Efficient Ring Opening of Epoxides Catalyzed by a New Electron Deficient Tin(IV) Porphyrin", Tetrahedron, Elsevier Science Publishers, Amsterdam, NL, vol. 60, No. 29, Jul. 12, 2004, pp. 6105-6111, XP004517643, ISSN: 0040-4020, DOI 10:1016/J.TET.2004.05.069.

* cited by examiner

US 9,663,432 B2

HIGH-PURITY MONOALKENYL-CONTAINING GLYCERIN DERIVATIVE AND METHOD OF MANUFACTURING SAME

RELATED APPLICATIONS

This application is the National Stage of International Patent Application No. PCT/JP2013/085004, filed on Dec. 26, 2013, which claims priority to and all the advantages of Japanese Patent Application No. 2012-289018, filed on Dec. 28, 2012, the content of which is incorporated herein by reference.

TECHNICAL FIELD

The present invention relates to a high-purity monoalkenyl-containing glycerin derivative and a method of manufacturing the same. Furthermore, the present invention relates to the use of a glycerin derivative-modified silicone in external use preparations, cosmetic compositions, and various industrial materials.

BACKGROUND ART

Conventionally, various modified silicone compounds are known as silicones having hydrophilic groups, and conventionally polyether-modified silicones have been used as nonionic silicones. There have also been disclosures of (poly)glycerin-modified silicone, and the like.

Monoalkenyl-containing glycerin derivatives, such as allyl diglycerin, are used as raw material for (poly)glycerin-modified silicone.

For example, Patent Document 1 describes that an allyl diglycerin is obtained as a monoalkenyl-containing glycerin derivative by reacting monoallyl glycerin, and the like, with glycidol. However, because allyl diglycerin is not ketalized, the product has a high boiling point and a high-purity product cannot be obtained by distillation. Therefore, because the product is not distilled, there are problems with low purity and residual ionic impurities, and the like.

Additionally, Patent Document 2 describes that allyl diglycerin ether is obtained as a monoalkenyl-containing glycerin derivative by reacting allyl glycidyl ether and glycerin with $BF_3$ as a catalyst. However, $BF_3$ is toxic and its use is not preferred. Additionally, because allyl diglycerin ether is not ketalized, the product has a high boiling point and a high-purity product cannot be obtained by distillation.

Meanwhile, Patent Document 3 describes that a polyglycerin compound having a ketal group is obtained using a glycidyl ether having a ketal group, but this does not use anything that would ketalize glycerin and does not yield a monoalkenyl-containing glycerin derivative.

Additionally, Patent Document 4 describes the production of a mono- or di-(akyl, alkenyl, or phenyl) ether to which a glycidyl ether is added, but does not use anything that would ketalize glycerin, and describes only a purification method with liquid separation in water. Moreover, the method does not yield a monoalkenyl-containing glycerin derivative.

Furthermore, Patent Document 5 describes reacting a ketalized or diacetalized polyglycerin and an alkylene oxide, and then deketalizing or deacetalizing the product, but this method does not yield a monoalkenyl-containing glycerin derivative. Butylene oxide is used as the alkylene oxide in Patent Document 5, but butylene oxide has poor hydrophilicity and different properties from a hydrophilic monoalkenyl-containing glycerin derivative, such as allyl diglycerin. Moreover, there is no disclosure of the purity of the product in Patent Document 5.

PRIOR ART DOCUMENT

Patent Document

Patent Document 1: Japanese Unexamined Patent Application Publication No. 2004-277548A
Patent Document 2: Japanese Unexamined Patent Application Publication No. H09-71504A
Patent Document 3: Japanese Unexamined Patent Application Publication No. H09-235247A
Patent Document 4: Japanese Unexamined Patent Application Publication No. 2004-105959A
Patent Document 5: Japanese Unexamined Patent Application Publication No. 2007-31554A
Patent Document 6: WO/2011/049248
Patent Document 7: WO/2011/049247
Patent Document 8: WO/2011/049246
Patent Document 9: Japanese Unexamined Patent Application Publication No. 2012-046507A
Patent Document 10: Japanese Unexamined Patent Application Publication No. 2013-151658A

SUMMARY OF INVENTION

Technical Problem

An object of the present invention is to provide a high-purity monoalkenyl-containing glycerin derivative, which has been difficult in the past.

Another object of the present invention is to provide a glycerin derivative-modified silicone that avoids or decreases the occurrence of thickening or gelation during production, is chemically stable, and further has excellent utility for its emulsifiability, dispersibility, and the like, and excellent formulation stability.

Yet another object of the present invention is to use such glycerin derivative-modified silicone in an external use preparation, cosmetic compositions, or various industrial materials.

Solution to Problem

An object of the present invention is achieved by a monoalkenyl-containing glycerin derivative with purity of not less than 92% and electrical conductivity of not greater than 50 µS/cm in 2.0 mass % aqueous solution at room temperature.

It is preferable that the monoalkenyl-containing glycerin derivative has purity of not less than 95% and electrical conductivity of not greater than 30 µS/cm in 2.0 mass % aqueous solution at room temperature.

It is more preferable that the monoalkenyl-containing glycerin derivative have purity of not less than 95% and electrical conductivity of not greater than 5 µS/cm in 2.0 mass % aqueous solution at room temperature.

It is preferable that the monoalkenyl-containing glycerin derivative is a monoalkenyl-containing diglycerin.

It is preferable that the monoalkenyl-containing glycerin derivative is manufactured by a manufacturing method comprising the following steps (A) through (C):
step (A): a step of reacting a ketalized glycerin derivative and a monoalkenyl glycidyl ether in the presence of an inorganic base to obtain a ketal of a monoalkenyl-containing glycerin derivative;

step (B): a step of purifying the ketal of monoalkenyl-containing glycerin derivative obtained in step (A) by distillation; and step (C): a step of hydrolyzing the ketal of monoalkenyl-containing glycerin derivative obtained in step (B) in the presence of an acid and an acidic inorganic salt.

It is preferable that the inorganic base is selected from the group consisting of alkali metal hydroxides, alkali earth metal hydroxides, alkoxides of alkali metals, alkoxides of alkali earth metals, and mixtures thereof.

It is more preferable that the acid in step (C) above is hydrochloric acid or trifluoroacetic acid.

It is preferable that the method further comprises a step (D) of removing the acid or acidic inorganic salt after step (C) above.

It is preferable that step (D) above includes stripping, specifically reduced pressure stripping.

An object of the present invention is also achieved by a silicone modifier comprising the monoalkenyl-containing glycerin derivative of the present invention, and by glycerin derivative-modified silicone modified with the monoalkenyl-containing glycerin derivative of the present invention.

An object of the present invention is also achieved by an external use preparation, cosmetic composition, or industrial material comprising the glycerin derivative-modified silicone of the present invention. It is preferable that the industrial material is a surface treatment agent or surfactant.

Advantageous Effects of Invention

The monoalkenyl-containing glycerin derivative of the present invention is highly pure and has very low content of ionic impurities, such as catalyst and salt. Therefore, when glycerin derivative-modified silicone is manufactured using the monoalkenyl-containing glycerin derivative of the present invention as a silicone modifier, unintended reactions with functional groups and side reactions, such as siloxane bond cleavage, can be avoided or decreased. Therefore, glycerin derivative-modified silicone can be stably manufactured by using the monoalkenyl-containing glycerin derivative of the present invention as an organic modifier.

Glycerin derivative-modified silicone modified with the monoalkenyl-containing glycerin derivative of the present invention avoids or decreases thickening or gelation, specifically thickening and gelation that can occur during production, and is chemically stable; and furthermore has excellent utility, such as emulsifiability and dispersability, and excellent formulation stability.

The glycerin derivative-modified silicone of the present invention can also be appropriately used as an external use preparation or cosmetic composition, and further can be widely used as various industrial materials.

Glycerin derivative silicone modified with the high-purity monoalkenyl glycerin derivative of the present invention exhibits excellent properties that allow it to be appropriately employed alone as a cosmetic raw material, such as an emulsifier, powder dispersing agent, powder surface treatment agent, or thickening agent, but because it also has good compatibility with various oils exemplified in this document, it can also be employed as cosmetic raw materials like those described above in the form of mixtures therewith. Above all, the glycerin derivative silicone of the present invention, particularly the diglycerin derivative-modified silicone of the present invention, is optimally employed as various cosmetic raw materials diluted with carprylyl methicone (FZ-3196, manufactured by Dow Corning). Dilution with carprylyl methicone improves the handling and production properties as a cosmetic raw material, while maintaining the properties of the modified silicone, and, as a multiplicative effect of both, additionally improves the affinity with ultraviolet absorbents and a wide range of oils, from silicone oil to a variety of organic oils, as well as the affinity with various powders. This improves the stability of cosmetic formulations, allows a broad range of flexibility (formulation and design freedom), and allows a variety of effects, such as improving coloring in color cosmetics, improving film transparency and improving SPF effect in skin care cosmetics as well. The suitable weight ratio of the two in mixture is carprylyl methicone:glycerin derivative silicone of the present invention=5:95 to 90:10. Designing a blend ratio in a range of 5:95 to 50:50 when the molecular weight or viscosity of the modified silicone is relatively low, or in a range of 50:50 to 90:10 when the molecular weight or viscosity of the modified silicone is relatively high, is preferable for the overall balance between performance and convenience.

DESCRIPTION OF EMBODIMENTS

A first aspect of the present invention is a high-purity monoalkenyl-containing glycerin derivative.

The first aspect of the present invention will be described in detail below.

<High-Purity Monoalkenyl-Containing Glycerin Derivative and Method of Manufacturing the Same>

The monoalkenyl-containing glycerin derivative of the present invention has purity of not less than 92% and electrical conductivity of not greater than 50 µS/cm in 2.0 mass % aqueous solution at room temperature. The monoalkenyl-containing glycerin derivative preferably has purity of not less than 95% and electrical conductivity of not greater than 30 µS/cm in 2.0 mass % aqueous solution at room temperature. Additionally, the monoalkenyl-containing glycerin derivative more preferably has purity of not less than 95% and electrical conductivity of not greater than 5 µS/cm in 2.0 mass % aqueous solution at room temperature.

In the present invention, "purity" is the purity of the glycerin derivative in the monoalkenyl-containing glycerin derivative, and is identified by peak area ratio of the various constituents in a gas chromatogram when the monoalkenyl-containing glycerin derivative is analyzed by gas chromatography and detected by a hydrogen flame ion detector (FID). The gas chromatograph used is not particularly limited, but, for example, GC-2010 manufactured by Shimadzu Corp. can be used.

In the present invention, "electrical conductivity" is the conductivity of the monoalkenyl-containing glycerin derivative, and corresponds to the quantity of ionic impurities contained in the monoalkenyl-containing glycerin derivative. The electrical conductivity in the present invention is measured at room temperature (20 to 25° C.), with the monoalkenyl-containing glycerin derivative in the form of a 2.0 mass % aqueous solution. The electrical conductivity measurement device is not particularly limited, but, for example, EC Meter CM-30G manufactured by DKK-Toa (Toa-denpa-kogyo) Corp can be used.

The monoalkenyl-containing glycerin derivative of the present invention is not particularly limited provided that it is a glycerin derivative having one alkenyl group. Examples of alkenyl groups include, for example, vinyl groups, allyl groups, butenyl groups, isobutenyl (methylyl) groups, 3,3-dimethylallyl groups, isoprenyl groups, and eugenyl groups, but vinyl groups and allyl groups are preferable, and allyl groups are more preferable.

The monoalkenyl-containing glycerin derivative of the present invention is a (poly)glycerin derivative having a reactive functional group, such as an alkenyl group, at the end of a molecular chain, such as monoallyl (poly) glycerin, and can be appropriately synthesized by a known method. Specifically, the monoalkenyl-containing glycerin derivative of the present invention is preferably a monoalkenyl-containing (poly)glycerin, such as monoallyl (poly)glycerin, more preferably a monoalkenyl-containing glycerin, such as allyl monoglycerin, a monoalkenyl-containing diglycerin, such as allyl diglycerin, or a monoalkenyl-containing triglycerin, such as allyl triglycerin, even more preferably a monoalkenyl-containing diglycerin, and particularly preferably an allyl diglycerin.

The monoalkenyl-containing glycerin derivative of the present invention can be manufactured by a manufacturing method comprising the following steps (A) through (C):

step (A): a step of reacting a ketalized glycerin derivative and a monoalkenyl glycidyl ether in the presence of an inorganic base to obtain a ketal of monoalkenyl-containing glycerin derivative;

step (B): a step of purifying the ketal of monoalkenyl-containing glycerin derivative obtained in step (A) by distillation; and step (C): a step of hydrolyzing the ketal of monoalkenyl-containing glycerin derivative obtained in step (A) with an acid and water.

In step (A), a ketalized glycerin derivative and a monoalkenyl glycidyl ether are reacted in the presence of a hydroxide of an alkali metal and/or alkali earth metal. A (poly)glycerin in which two hydroxyl groups of the three hydroxyl groups at glycerin moiety of (poly)glycerin are ketalized can be used as the ketalized glycerin derivative. For example, when ketalizing glycerin, 2,2-dimethyl-1,3-dioxolane-4-methanol represented by the following structural formula (1):

[Formula 1]

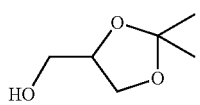

(1)

can be used as the ketalized glycerin derivative. In this structural formula, it is desirable that the purity of ketalized glycerin derivative represented by (1) is not less than 97%, and the remaining impurities may be ketalized glycerin derivatives represented by the following structural formula (2):

[Formula 2]

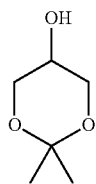

(2)

It is preferred that the alkenyl group in the monoalkenyl glycidyl ether is an allyl group, as described above. Therefore, an allyl glycidyl ether represented by the following structural formula:

[Formula 3]

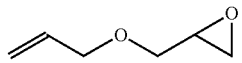

is preferred as a monoalkenyl glycidyl ether.

Consequently, in step (A), when 2,2-dimethyl-1,3-dioxolane-4-methanol is used as the ketalized glycerin derivative and allyl glycidyl ether is used as the monoalkenyl glycidyl ether, a monoallyl diglycerol dimethylketal represented by the following structural formula:

[Formula 4]

(3-1)

(3-2)

(3-3)

(3-4)

is obtained as a ketal of monoalkenyl-containing glycerin derivative.

The inorganic base is not particularly limited, but examples thereof include hydroxides of alkali metals, hydroxides of alkali earth metals, carbonates such as $Li_2CO_3$, $Na_2CO_3$, $K_2CO_3$, $Cs_2CO_3$, $CaCO_3$, and $BaCO_3$, bicarbonates such as $NaHCO_3$ and $KHCO_3$, and oxides such as $Li_2O$, $Na_2O$ $K_2O$, $CaO$, and $BaO$. It is preferable that the inorganic base be selected from the group consisting of alkali metal hydroxides, alkali earth metal hydroxides, alkoxides of alkali metals, alkoxides of alkali earth metals, and mixtures thereof.

Examples of hydroxides of alkali metals include lithium hydroxide, sodium hydroxide, potassium hydroxide, and cesium hydroxide. Examples of hydroxides of alkali earth metals include magnesium hydroxide and calcium hydroxide. Hydroxides of alkali metals or hydroxides of alkali earth metals each may be used independently, or may be mixtures of two or more thereof. Mixtures of alkali metal hydroxides and alkali earth metal hydroxides may also be used.

Examples of the alkoxides of alkali metals and/or alkali earth metals include methoxides, ethoxides, and butoxides, but methoxides are preferable. Alkali metal alkoxides or alkali earth metal alkoxides each may be used independently, or may be mixtures of two or more thereof. Mixtures of alkali metal alkoxides and alkali earth metal alkoxides may also be used.

In step (B), the ketal of monoalkenyl-containing glycerin derivative obtained in step (A) is purified by distillation. The ketal of monoalkenyl-containing glycerin derivative can be easily purified by distillation to a high level of purity because it is ketalized and has a relatively low boiling point.

Distillation can be performed by a known method. However, it is preferable to perform distillation in a reduced pressure state to lower the temperature as much as possible in order to suppress decomposition of the ketal of monoalkenyl-containing glycerin derivative. The distillation pressure is, for example, not less than 0.01 mmHg and not greater than 100 mmHg, but not greater than 50 mmHg is preferable, and not greater than 10 mmHg is more preferable. Additionally, an example distillation temperature is 60 to 200° C., preferably 100 to 190° C., and more preferably 120 to 180° C. Furthermore, the reaction system may be neutralized before distillation by adding an acid, described below.

In step (C), the ketal of monoalkenyl-containing glycerin derivative obtained in step (B) is hydrolyzed in the presence of an acid and/or acidic inorganic salt. The acid is not particularly limited, and various types of inorganic acids or organic acids can be used. Examples of inorganic acids include hydrochloric acid, sulfuric acid, nitric acid, phosphoric acid, boric acid, hydrobromic acid, and hydrofluoric acid, but hydrochloric acid is preferable. Examples of organic acids include carboxylic acid and sulfonic acid, of which water-soluble carboxylic acid is preferable, formic acid, acetic acid, trichloroacetic acid, and trifluoroacetic acid, of which trifluoroacetic acid is more preferable. The acidic inorganic salts are not particularly limited and various types of acidic inorganic salts can be used, but acidic inorganic salts can be used in which at least the monovalent hydrogen atom of at least divalent inorganic acid is neutralized with a base. Examples of the inorganic acid that is at least divalent include sulfuric acid, sulfurous acid, and the like. Examples of the base include an alkali metal, ammonia, and the like. Typically, lithium hydrogensulfate, sodium hydrogensulfate, potassium hydrogensulfate, rubidium hydrogensulfate, cesium hydrogensulfate, ammonium hydrogensulfate, sodium hydrogen sulfite, or hydrates thereof are given as examples of acidic inorganic salts.

Therefore, when monoallyl diglycerol dimethyl ketal is used as the ketal of monoalkenyl-containing glycerin derivative in step (C), a monoallyl diglycerol represented by the following formula:

[Formula 5]

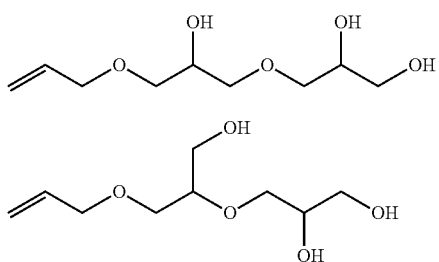

(4-1)

(4-2)

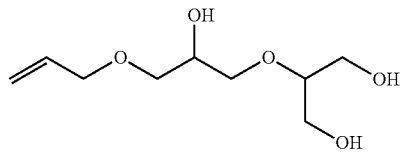

(4-3)

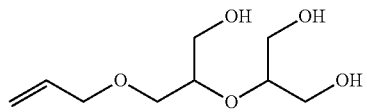

(4-4)

is obtained as the monoalkenyl-containing glycerin derivative of the present invention.

It is preferable that the above manufacturing method further includes a step (D) of removing the acid or acidic inorganic salt after step (C). The removal method is not particularly limited and neutralization or extraction using the various inorganic bases, or the like, can be listed as examples thereof, but removal by stripping, particularly reduced pressure stripping, is preferable.

The monoalkenyl-containing glycerin derivative of the present invention obtained by the above manufacturing method can have high purity of not less than 92%, and electrical conductivity of not greater than 50 μS/cm, preferably not greater than 30 μS/cm, in 2.0 mass % aqueous solution at room temperature. In particular, when acid is used in step (C), purity of not less than 95% can be achieved. When the method comprises an acid removal step (D) after the step (C), and acid is removed in step (D) by stripping, electrical conductivity can be achieved of not greater than 5.0 μS/cm in 2.0 mass % aqueous solution at room temperature.

A second aspect of the present invention is a glycerin derivative-modified silicone modified with the high-purity monoalkenyl-containing glycerin derivative.

The second aspect of the present invention will be described in detail below.

<Glycerin Derivative-Modified Silicone and Method of Manufacturing the Same>

The high-purity monoalkenyl-containing glycerin derivative can be used to organically modify silicone, and in particular, can be appropriately used to modify silicone by a hydrosilylation reaction. Therefore, the high-purity monoalkenyl-containing glycerin derivative can be used as a silicone modifier, and specifically as a hydrosilylation reactive silicone modifier.

The glycerin derivative-modified silicone that is modified with the high-purity monoalkenyl-containing glycerin derivative is not particularly limited and, for example, is a glycerin derivative-modified silicone represented by the following general formula (1):

[Formula 6]

$$R^1_a R^2_b L^1_c Q_d SiO_{(4-a-b-c-d)/2} \quad (1)$$

(wherein $R^1$ represents a monovalent organic group (however, excluding $R^2$, L, and Q), a hydrogen atom or a hydroxyl group; and $R^2$ is a substituted or unsubstituted, straight or branched monovalent hydrocarbon group having from 9 to 60 carbon atoms, or a chain organosiloxane group represented by the following general formula (2-1):

[Formula 7]

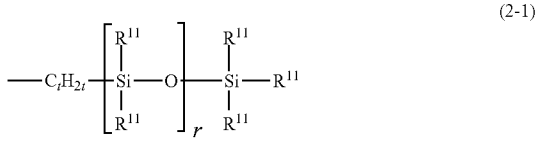

(2-1)

(wherein $R^{11}$ are each independently a substituted or unsubstituted monovalent hydrocarbon group having from 1 to 30 carbon atoms, hydroxyl groups, or hydrogen atoms and at least one of the $R^{11}$ moieties is the monovalent hydrocarbon group; t is a number in a range of 2 to 10; and r is a number in a range of 1 to 500); or the general formula (2-2) below:

[Formula 8]

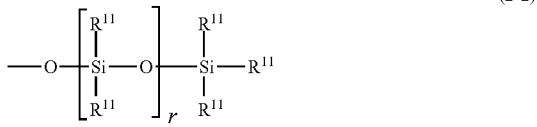

(2-2)

(wherein, $R^{11}$ and r are synonymous with those described above); and $L^1$ represents a silylalkyl group having a siloxane dendron structure represented by the following general formula (3) when i=1;

[Formula 9]

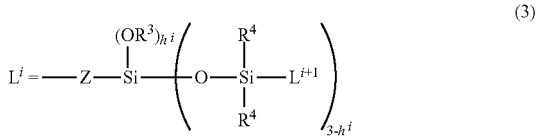

(3)

(wherein $R^3$ each independently represents a substituted or unsubstituted, straight or branched monovalent hydrocarbon group having from 1 to 30 carbon atoms, $R^4$ each independently represents an alkyl group or phenyl group having from 1 to 6 carbon atoms, Z represents a divalent organic group, i represents the generation of a silylalkyl group indicated by $L^i$, and is an integer 1 to k, where k is the number of generations that is the number of repetitions of the silylalkyl group, the number of generations k is an integer from 1 to 10, $L^{i+1}$ is the silylalkyl group when i is less than k, and is $R^4$ when i=k, and $h^i$ is a number in a range of 0 to 3); and Q represents a glycerin derivative group; and a, b, c, and d are numbers in the ranges so that $1.0 \leq a \leq 2.5$, $0 \leq b \leq 1.5$, $0 \leq c \leq 1.5$, and $0.0001 \leq d \leq 1.5$.

Here, when the glycerin derivative-modified silicone represented by general formula (1) has the long chain organic group or the chain organosiloxane group represented by $R^2$, b is a number greater than 0, preferably $0.0001 \leq b \leq 1.5$, and more preferably $0.001 \leq b \leq 1.5$. Similarly, when the glycerin derivative-modified silicone represented by general formula (1) has a silylalkyl group having a siloxane dendron structure represented by $L^1$, it is preferable that c is a number greater than 0 and $0.0001 \leq c \leq 1.5$, more preferably $0.001 \leq c \leq 1.5$.

It is preferable that the glycerin derivative-modified silicone has the glycerin derivative group (Q) and has a long-chain organic group or chain organosiloxane group represented by $R^2$, or a silylalkyl group having a siloxane dendron structure represented by $L^1$.

At this time, the suitable values of b and c are represented as follows by essential functional groups.

(1) When there is a group represented by $R^2$: $0.001 \leq b \leq 1.5$ and $0 \leq c \leq 1.5$.

(2) When there is a group represented by $L^1$: $0 \leq b \leq 1.5$ and $0.001 \leq c \leq 1.5$.

(3) When there are both a group represented by $R^2$ and a group represented by $L^1$: $0.001 \leq b \leq 1.5$ and $0.001 \leq c \leq 1.5$.

The monovalent organic groups, which are $R^1$ of general formula (1), can be the same or different, and they are not particularly limited provided that they are not a functional group of $R^2$, $L^1$, and Q. However, they preferably are a substituted or unsubstituted, straight or branched monovalent hydrocarbon group having from 1 to 8 carbon atoms, a polyoxyalkylene group represented by $-R^5O(AO)_nR^6$ (wherein AO represents an oxyalkylene group having from 2 to 4 carbon atoms; $R^5$ represents a substituted or unsubstituted, straight or branched divalent hydrocarbon group having from 3 to 5 carbon atoms; $R^6$ represents a substituted or unsubstituted, straight or branched monovalent hydrocarbon group having from 1 to 24 carbon atoms and hydrogen atoms, or a substituted or unsubstituted, straight or branched acyl group having from 2 to 24 carbon atoms; and n is 1 to 100), an alkoxy group, a (meth)acryl group, an amide group, a carbinol group, or a phenolic group. However, not all $R^1$ become a hydroxyl group, a hydrogen atom, the alkoxy group, or the polyoxyalkylene group.

Examples of a monovalent hydrocarbon group having from 1 to 8 carbon atoms are, for example, alkyl groups such as a methyl group, ethyl group, propyl group, butyl group, pentyl group, hexyl group, heptyl group, octyl group, and the like; cycloalkyl groups such as a cyclopentyl group, cyclohexyl group, and the like; alkenyl groups such as a vinyl group, allyl group, butenyl group, and the like; aryl groups such as a phenyl group, tolyl group, and the like; aralkyl groups such as a benzyl group; and groups wherein the hydrogen atoms bonded to the carbon atoms of these groups are substituted at least partially by fluorine or a similar halogen atom, or an organic group having an epoxy group, a glycidyl group, an acyl group, a carboxyl group, an amino group, a (meth)acryl group, a mercapto group, or the like (however, the total number of carbon atoms is from 1 to 8). The monovalent hydrocarbon group is preferably a group other than an alkenyl group, and is particularly preferably a methyl group, an ethyl group, or a phenyl group. Additionally, examples of the alkoxy group include a methoxy group, an ethoxy group, an isopropoxy group, a butoxy group, and similar lower alkoxy groups; a lauryl alkoxy group, a myristyl alkoxy group, a palmityl alkoxy group, an oleyl alkoxy group, a stearyl alkoxy group, a behenyl alkoxy group, and similar higher alkoxy groups; and the like.

Particularly, the $R^1$ moieties are preferably monovalent hydrocarbon groups having from 1 to 8 carbon atoms and that do not have unsaturated aliphatic bonds or monovalent fluorinated hydrocarbon groups. Examples of the monovalent hydrocarbon group not having unsaturated aliphatic bonds belonging to the $R^1$ moiety include methyl groups, ethyl groups, propyl groups, butyl groups, pentyl groups, hexyl groups, and similar alkyl groups; phenyl groups, tolyl groups, xylyl groups, and similar aryl groups; and aralkyl groups such as benzyl groups. Examples of the monovalent fluorinated hydrocarbon group include trifluoropropyl groups, pentafluoroethyl groups, and similar perfluoroalkyl groups. From an industrial perspective, $R^1$ is preferably a methyl group, an ethyl group, or a phenyl group, and more preferably from 90 mol % to 100 mol % of all the $R^1$ moieties are selected from methyl groups, ethyl groups, or phenyl groups.

A glycerin derivative-modified silicone aims at imparting additional functionality, and it is possible to introduce or design a modified group other than a hydrophilic group (-Q), particularly a short chain or medium chain hydrocarbon based group, as $R^1$. Specifically, when $R^1$ is a substituted monovalent hydrocarbon group, a substituent can be preferably selected in accordance with desired characteristics and uses. For example, when used as a cosmetic composition or fiber treatment agent raw material, a monovalent hydrocarbon substituent group, such as an amino group, amide group, aminoethyl aminopropyl group, an a carboxyl group, can be introduced for the purpose of improving the feel during use, tactile feel, persistence and the like.

The substituted or unsubstituted, straight or branched monovalent hydrocarbon group having from 9 to 60 carbon atoms of $R^2$ of general formula (1) is a long chain hydrocarbon group or a chain organosiloxane group represented by general formula (2-1) or (2-2). By introducing this group at the main chain and/or side chain of polysiloxane, it is possible to further improve the affinity, emulsifiability, and dispersibility, and further the sensation during use of various components such as an oil agent, powder, or the like incorporated in an external use preparation or a cosmetic composition. Furthermore, because the monovalent long chain hydrocarbon group or chain organopolysiloxane group is a hydrophobic functional group, the compounding stability and the compatibility with organic oils having a high content of alkyl groups are further improved. $R^2$ may be all the monovalent long chain hydrocarbon group or all the chain organopolysiloxane group, or may be a functional group of both of these groups. In the glycerin derivative-modified silicone, it is particularly preferable that part or all of $R^2$ is a monovalent long chain hydrocarbon group, and by having such a monovalent long chain hydrocarbon group in a molecule, the glycerin derivative-modified silicone exhibits more superior compatibility not only with silicone oil, but with non silicone oil with a high alkyl group content as well. For example, it is possible to obtain an emulsion and a dispersion with superior stability over time and thermal stability, which are made of non silicone oil.

Substituted or unsubstituted, straight or branched monovalent hydrocarbon groups that are represented by $R^2$ of general formula (1), that are bonded to silicon atoms, and that have from 9 to 60 carbon atoms, may be the same or different. Furthermore, the structure thereof is selected from among straight, branched, and partially branched structure. In the present invention, it is particularly preferable for $R^2$ to be an unsubstituted straight monovalent hydrocarbon group. An unsubstituted monovalent hydrocarbon group can be, for example, an alkyl group, aryl group, or aralkyl group having from 9 to 60 carbon atoms, preferably 9 to 30 carbon atoms, and more preferably 10 to 25 carbon atoms. On the other hand, examples of the substituted monovalent hydrocarbon group include perfluoroalkyl groups, aminoalkyl groups, amide alkyl groups, and carbinol groups having from 9 to 30 carbon atoms, preferably from 9 to 30 carbon atoms, and more preferably from 10 to 24 carbon atoms. Additionally, the carbon atoms of the monovalent hydrocarbon groups may be partially substituted with alkoxy groups, and examples of said alkoxy groups include methoxy groups, ethoxy groups, and propoxy groups. This type of monovalent hydrocarbon group is particularly preferably an alkyl group having from 9 to 30 carbon atoms, and an example thereof is a group represented by the general formula $—(CH_2)_v—CH_3$ (v is a number in a range of 8 to 29). Particularly, an alkyl group having from 10 to 24 carbon atoms is preferable.

The chain organosiloxane group in general formula (2-1) or (2-2) has a straight polysiloxane chain structure, unlike a silylalkyl group, which has a siloxane dendron structure. In general formula (2-1) or (2-2), $R^{11}$ are each independently a substituted or unsubstituted monovalent hydrocarbon group having from 1 to 30 carbon atoms, a hydroxyl group, or a hydrogen atom. The substituted or unsubstituted monovalent hydrocarbon group having from 1 to 30 carbon atoms is preferably an alkyl group having from 1 to 30 carbon atoms, an aryl group having from 6 to 30 carbon atoms, an aralkyl group having from 6 to 30 carbon atoms, or a cycloalkyl group having from 6 to 30 carbon atoms, and is exemplified by a methyl group, ethyl group, propyl group, butyl group, pentyl group, hexyl group, heptyl group, octyl group, decyl group, or other alkyl group; a cyclopentyl group, cyclohexyl group, or other cycloalkyl group; or a phenyl group, tolyl group, or other aryl group. The hydrogen atoms bonded to the carbon atoms of these groups may be substituted at least partially by fluorine or a similar halogen atom, or an organic group containing an epoxy group, acyl group, carboxyl group, amino group, methacryl group, mercapto group, or the like. A methyl group, a phenyl group, or a hydroxyl group is particularly preferable as $R^{11}$. A configuration in which a part of $R^{11}$ is a methyl group and another part of $R^{11}$ is a long chain alkyl group having from 8 to 30 carbon atoms is also preferable.

In general formula (2-1) or (2-2), r is a number in a range of 2 to 10; r is a number in a range of 1 to 500; and r preferably is a number in a range of 2 to 500. Such a straight-chain organosiloxane group is hydrophobic. From the standpoint of compatibility with various oil agents, r preferably is a number in a range of 1 to 100, and particularly preferably is a number in a range of 2 to 30.

A silylalkyl group having a siloxane dendron structure represented by general formula (3) is a functional group that includes a structure in which a carbosiloxane unit spreads in a dendrimer shape and that exhibits high water repellence. The silylalkyl group is well-balanced when combined with hydrophilic groups, and when an external use preparation or cosmetic composition that incorporates the glycerin derivative-modified silicone is used, the silylalkyl group inhibits an unpleasant sticky feeling, and provides a refreshingly natural feeling to the touch. Additionally, the silylalkyl group having a siloxane dendron structure is chemically stable, and for this reason, the silylalkyl group is a functional group providing advantageous properties such as usability in combination with a wide range of components.

Examples of the substituted or unsubstituted, straight or branched monovalent hydrocarbon group having from 1 to 30 carbon atoms (the $R^3$ moieties in general formula (3)) include methyl groups, ethyl groups, propyl groups, butyl groups, pentyl groups, hexyl groups, heptyl groups, octyl groups, and similar alkyl groups; cyclopentyl groups, cyclohexyl groups, and similar cycloalkyl groups; vinyl groups, allyl groups, butenyl groups, and similar alkenyl groups; phenyl groups, tolyl groups, and similar aryl groups; benzyl groups and similar aralkyl groups; and groups wherein the hydrogen atoms bonded to the carbon atoms of these groups are substituted at least partially by fluorine or a similar halogen atom, or an organic group containing an epoxy group, a glycidyl group, an acyl group, a carboxyl group, an amino group, a methacryl group, a mercapto group, or the like (provided that the total number of carbon atoms is from 1 to 30).

Among the phenyl group or the alkyl group having from 1 to 6 carbon atoms represented by $R^4$ in general formula (3), examples of the alkyl group having from 1 to 6 carbon atoms include methyl, ethyl, n-propyl, i-propyl, n-butyl, i-butyl, s-butyl, pentyl, neopentyl, cyclopentyl, hexyl, and similar straight, branched, or cyclic alkyl groups.

In the general formula (3), when i=k, $R^4$ is preferably a methyl group or a phenyl group. In particular, R4 is preferably a methyl group when i=k.

From an industrial standpoint, the number of generations k is preferably an integer from 1 to 3, and more preferably is 1 or 2. In each of the number of generations, the group represented by $L^1$ is represented as follows. In the formulae, $R^3$, $R^4$, and Z are groups synonymous with the group described above.

When the number of generations is k=1, $L^1$ is represented by the following general formula (3-1).

[Formula 10]

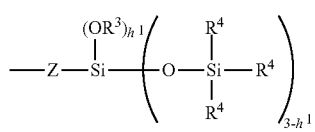

(3-1)

When the number of generations is k=2, $L^1$ is represented by the following general formula (3-2).

[Formula 11]

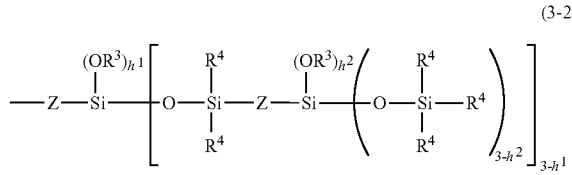

(3-2)

When the number of generations is k=3, $L^1$ is represented by the following general formula (3-3).

[Formula 12]

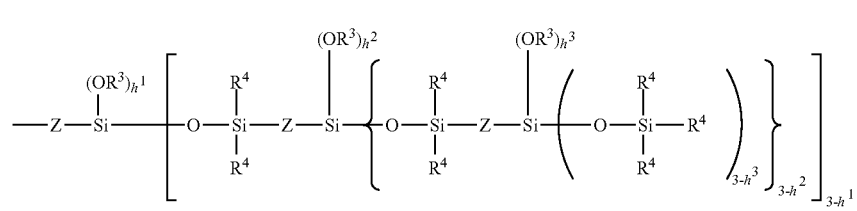

(3-3)

In the structures represented by the general formulae (3-1) to (3-3) in the case of the number of generations is from 1 to 3, each of $h^1$, $h^2$ and $h^3$ moieties is independently a number in a range of 0 to 3. These $h^i$ moieties are preferably a number in a range of 0 to 1, and $h^i$ is, in particular, preferably 0.

In general formulae (3) and (3-1) to (3-3), Z are each independently a divalent organic group, and specific examples thereof include a divalent organic group formed by addition-reacting a silicon-bonded hydrogen atom and a functional group having an unsaturated hydrocarbon group such as an alkenyl group, an acryloxy group, a methacryloxy group, or the like at the terminal. Depending on the method for introducing the silylalkyl group having a siloxane dendron structure, the functional group can be appropriately selected and is not restricted to the functional groups described above. Preferably, Z are each independently a group selected from divalent organic groups represented by the following general formula.

[Formula 13]

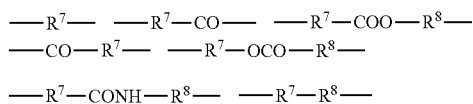

Of these, Z in $L^1$ is preferably a divalent organic group represented by general formula —$R^7$— that is introduced by a reaction between a silicon-bonded hydrogen atom and an alkenyl group. Likewise, Z is preferably a divalent organic group represented by general formula —$R^7$—COO—$R^8$— that is introduced by a reaction between a silicon-bonded hydrogen atom and an unsaturated carboxylic ester group.

On the other hand, in the silylalkyl group represented by $L^i$, in which the number of generations k is not less than 2, and $L^i$ is $L^2$ to $L^k$, Z is preferably an alkylene group having from 2 to 10 carbon atoms and, in particular, is preferably a group selected from an ethylene group, a propylene group, a methylethylene group, and a hexylene group, and most preferably is an ethylene group.

In the general formula described above, $R^7$ are each independently a substituted or unsubstituted straight or branched alkylene group or alkenylene group having from 2 to 22 carbon atoms or an arylene group having from 6 to 22 carbon atoms. More specifically, examples of $R^7$ include an ethylene group, a propylene group, a butylene group, a hexylene group, and similar straight-chain alkylene groups; a methylmethylene group, a methylethylene group, a 1-methylpentylene group, a 1,4-dimethylbutylene group, and similar branched alkylene groups. $R^7$ is preferably a group selected from an ethylene group, a propylene group, a methylethylene group, and a hexylene group.

In the general formula described above, $R^8$ is a group selected from divalent organic groups represented by the following formula.

[Formula 14]

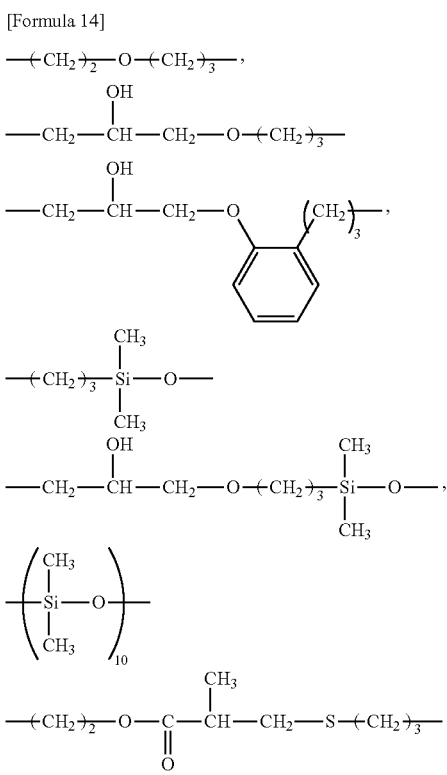

In general formula (1), Q is a glycerin derivative group, and forms the hydrophilic site of the glycerin derivative-modified silicone. The structure of Q is not limited provided that the structure has a glycerin derivative site, but the glycerin derivative residue is preferably bonded to the silicon atom via a divalent organic group.

The glycerin derivative residue here is a hydrophilic group having a (poly)glycerin structure, preferably a hydrophilic group having a monoglycerin, diglycerin, triglycerin, tetraglycerin, or at least pentamer polyglycerin structure. Monoglycerin, diglycerin, and triglycerin are more preferable, and diglycerin are especially more preferable. Additionally, the terminal hydroxyl group may be partially capped with an alkyl group. Furthermore, the (poly)glycerin structure may be straight or branched, and may be a structure that is branched in a dendritic manner as well.

The glycerin derivative group (Q) described above is preferably bonded to a silicon atom via a linking group that is at least divalent and is preferably a glycerin derivative group comprising at least one type of hydrophilic unit selected from hydrophilic units represented by structural formulae (3-3) to (3-6) below. The hydrophilic units that constitute Q do not consist solely of the following structural formula (3-6).

[Formula 15]

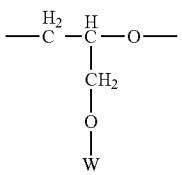 (3-3)

[Formula 16]

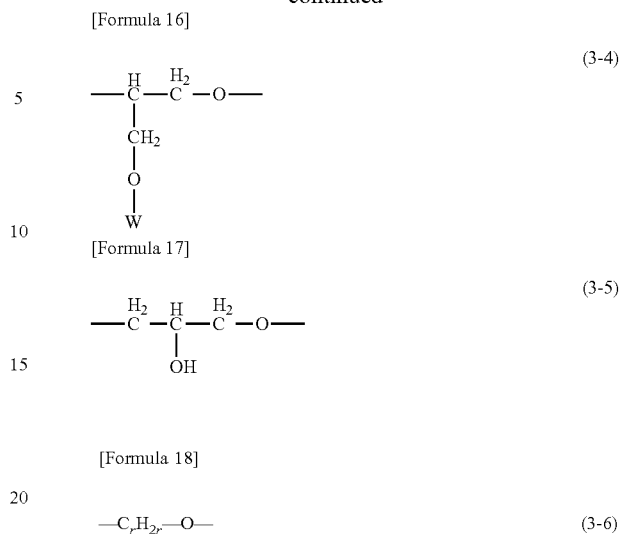

r is a number in a range of 1 to 6.

In formulae (3-3) to (3-5), W is a hydrogen atom or an alkyl group having from 1 to 20 carbon atoms, and preferably is a hydrogen atom. Particularly, when W is a hydrogen atom, oxidation in air does not occur easily, and aldehydes such as formaldehyde and the like, and antigenic compounds such as formate esters and the like, are not easily produced over time while in storage. Therefore, when W is a hydrogen atom, there is a benefit of high environmental compatibility.

The hydrophilic units represented by structural formulae (3-3) to (3-5) are hydrophilic units included in a hydrophilic group derived from a hydrophilic compound selected principally from polyhydric alcohols including glycerin, polyglycerins (also called "polyglycerols"), and polyglycidyl ethers or compounds in which terminal hydroxyl groups thereof are partially capped by hydrocarbon groups. Furthermore, the glycerin derivative group (Q) of the present invention may be a hydrophilic group that optionally comprises a hydrophilic structure (polyether structure) consisting of an oxyalkylene unit represented by the above structural formula (3-6) (for example, oxyethylene unit or oxypropylene unit).

In the general formula (1), Q may be, for example, a hydrophilic group that does not have a branched structure such as a monoglycerin-modified group or a diglycerin-modified group, and may also be a hydrophilic group that has a partial branched structure in the functional group such as a polyglycerol group or a polyglycidylether group.

In further detail, Q may also be glycerin derivative group made by bonding at least one hydrophilic unit selected from the hydrophilic units represented by the above structural formulae (3-3) to (3-6) in a straight chain, and that are bound to a silicon atom via at least divalent linking groups (provided that the hydrophilic unit that constitutes Q is made not only from the structural formula (3-6)). Similarly, Q may also be a glycerin derivative that contains at least two of at least one hydrophilic unit selected from the hydrophilic units represented by the above structural formulae (3-3) to (3-6), and that are bonded to a silicon atom via at least divalent linking groups, and that has a branching unit selected from groups represented by structural formulae (3-7) to (3-9) below.

[Formula 19]

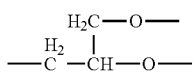
(3-7)

[Formula 20]

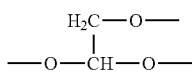
(3-8)

[Formula 21]

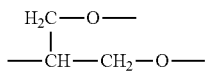
(3-9)

In structural formulae (3-7) to (3-9), the at least one hydrophilic unit selected from the hydrophilic units represented by the general formulae (3-3) to (3-6) are each independently bonded to the two oxygen atoms. The hydrophilic unit may further be bonded to a branch unit selected from groups represented by structural formulae (3-7) to (3-9). Moreover, the hydrophilic unit may be formed so as to have a dendroid-shape polyether structure, a polyglycerol structure, or a polyglycidyl ether structure obtained by branching into multiple generations. For example, the structure of a hydrophilic group Q which has one branch unit represented by structural formula (3-7) and two branch units represented by structural formula (3-9) and which is branched in a dendritic manner is shown below, but it goes without saying that dendroid-shape polyglycerol structures are not limited to this example.

(wherein m is a number in a range of 0 to 50, provided that not all of the m moieties are 0).

The linking group that is at least divalent is a bonding site with respect to the silicon atom included in the hydrophilic group Q, and a structure thereof is not particularly limited. Examples thereof include, ethylene groups, propylene groups, butylene groups, hexylene groups, and similar alkylene groups; ethylene phenylene groups, propylene phenylene groups, and similar alkylene phenylene groups; ethylene benzylene groups and similar alkylene aralkylene groups; ethyleneoxy phenylene groups, propyleneoxy phenylene groups, and similar alkyleneoxy phenylene groups; methyleneoxy benzylene groups, ethyleneoxy benzylene groups, propyleneoxy benzylene groups, and similar alkyleneoxy benzylene groups; and, furthermore, groups described below. Note that there are preferably from 0 to 3 and more preferably 0 or 1 ether bonds in the linking group that is at least divalent.

[Formula 23]

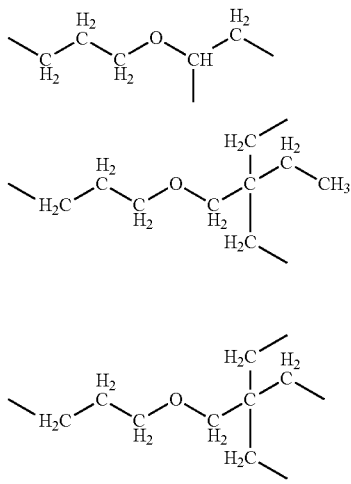

[Formula 22]

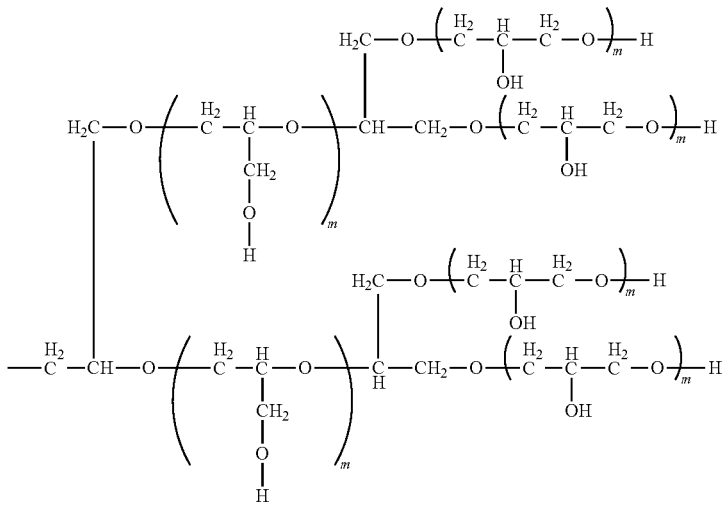

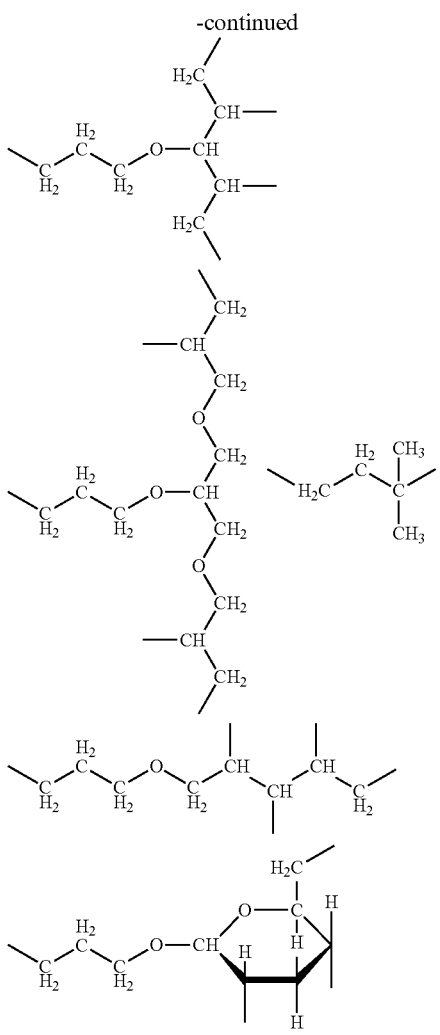

More preferably, Q is a hydrophilic group represented by structural formulae (4-1) to (4-4) below, and these are generally hydrophilic groups derived from polyglycerin-based compounds.

[Formula 24]

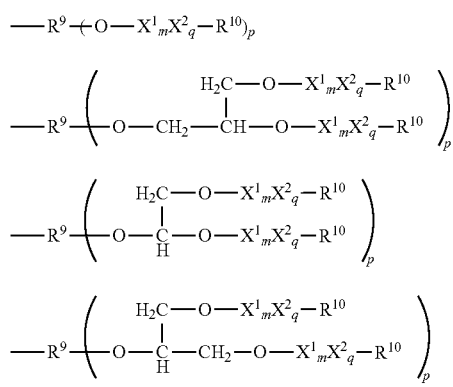

In formulae (4-1) to (4-4), $R^9$ is an organic group having (p+1) valence, and p is a number that is greater than or equal to 1 and less than or equal to 3. As the $R^9$, the same groups as the linking group that is at least divalent; may be given as an example.

It is more preferable that p is equal to 1 and that $R^9$ is a group selected from divalent organic groups represented by the following general formulae

[Formula 25]

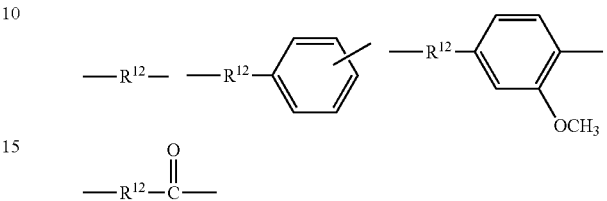

(wherein $R^{12}$ may have a substituent, and are each independently a straight or branched alkylene group or alkenylene group having from 2 to 22 carbon atoms, or an arylene group having from 6 to 22 carbon atoms).

$X^1$ are each independently at least one hydrophilic unit selected from the hydrophilic units represented by general formulae (3-3-1) to (3-5-1) below, and m is a number in a range of 1 to 5, and is more preferably a number in a range of 1 to 4.

[Formula 26]

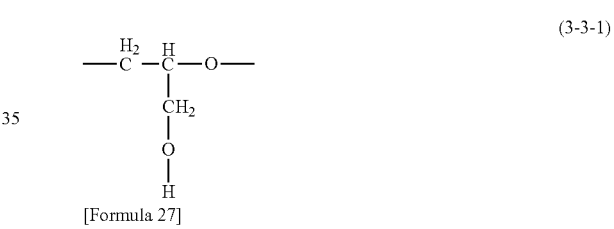

[Formula 27]

[Formula 28]

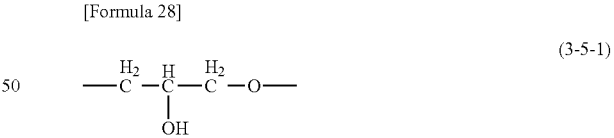

$X^2$ is any (poly)oxyethylene unit that Q may contain, and q is a number in the range 0 to 500. In the present invention, it is preferable that Q is a glycerin derivative group and q is a number in the range 1 to 500, more preferably a number in the range 2 to 300, and even more preferably a number in the range 2 to 100. Furthermore, $X^2$ may, in addition to a (poly)oxyethylene unit, also include a (poly)oxypropylene unit and/or (poly)oxybutylene unit. In this case, $X^2$ can be included in Q as a (poly)oxyalkylene unit represented by the unit represented by the formula: $-(C_2H_4O)_{t1}(C_3H_6O)_{t2}(C_4H_8O)_{t3}-$ (wherein t1, t2, and t3 are numbers where $1 \leq t1 \leq 500$, $0 \leq t2 \leq 100$, and $0 \leq t3 \leq 10$, preferably numbers where $2 \leq t1 \leq 300$, $0 \leq t2 \leq 50$, and $0 \leq t3 \leq 5$, and more preferably numbers where $2 \leq t1 \leq 100$, $0 \leq t2 \leq 10$, and $0 \leq t3 \leq 3$).

Here, the manner in which $X^1$ and $X^2$ are bonded can be block or random. That is, the hydrophilic group Q may be a hydrophilic group in which hydrophilic segments, which are obtained by bonding hydrophilic units represented by general formulae (3-3-1) to (3-5-1) above in a block manner, are bonded to hydrophilic segments comprising polyoxyalkylene units, and may be a hydrophilic group in which these constituent units are bonded in a random manner. An example thereof is a bonding pattern such as $—(X^2)_{m1}—X^1—(X^2)_{m2}—X^1—$.

$R^{10}$ is a hydrogen atom or a group selected from the group consisting of glycidyl groups, acyl groups, and alkyl groups having from 1 to 20 carbon atoms.

From the aspect of the thickening effect and gelation properties on oil ingredients, and the surfactant properties, such as emulsion and dispersion stability, of the glycerin derivative-modified silicone of the present invention, a suitable hydrophilic group Q is a hydrophilic group that is introduced from a (poly)glycerin represented by the following structural formula (4-1-1).

[Formula 29]

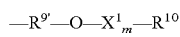
(4-1-1)

In the formula, $R^{9'}$ is a divalent organic group, and can be a group synonymous with the group described above. $X^1$ and $R^{10}$ are groups synonymous with the group described above, and m is a number in a range of 1 to 5.

From the viewpoints of the thickening effect and gelation properties on oil ingredients, and use as a surfactant (emulsifier), moisturizing agent, and various treatment agents (powder dispersant or surface treatment agent), especially of use as a powder preparation agent and use as a cosmetic raw material, it is most preferable that the hydrophilic group Q is a hydrophilic group derived from the monoalkenyl-containing glycerin derivative of the present invention that is a hydrophilic group derived from a (poly)glycerin. Specifically, the hydrophilic group Q is a (poly)glycerinmonoallyl ether or a (poly)glyceryl eugenol, which are examples of hydrophilic groups derived from (poly)glycerin compounds having a monoglycerin, diglycerin, triglycerin, or tetraglycerin structure.

An especially suitable hydrophilic group Q is a diglycerin derivative group in which the average number of repetitions m of the glycerin unit in the structural formula (4-1-1) is a number in a range of 1.5 to 2.4. At this time, $R^{9'}$ in the formula is a divalent organic group, and can be a group synonymous with the group described above. $X^1$ and $R^{10}$ are groups synonymous with the group described above.

The most suitable diglycerin derivative group is a diglycerin derivative group represented by the following general formula (5-1):

[Formula 30]

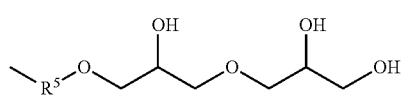
(5-1)

(wherein, $R^5$ is a divalent organic group that does not have an oxyalkylene structure wherein an average value of the number of repetitions of the oxyalkylene unit is two or more) or the following general formula (5-2):

[Formula 31]

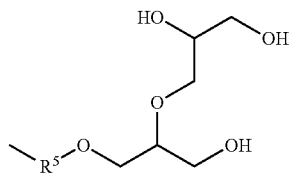
(5-2)

(wherein, $R^5$ is the same as above), or by the following general formula (5-3):

[Formula 32]

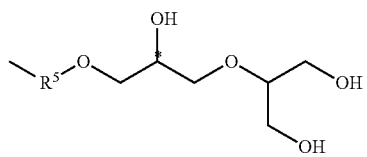
(5-3)

(wherein, $R^5$ is the same as above), or by the following general formula (5-4):

[Formula 33]

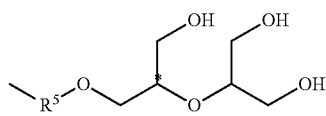
(5-4)

(wherein, $R^5$ is the same as above).

The bonding site of the glycerin derivative group (-Q) may be either a side chain or terminal of the polysiloxane main chain, the structure may be have two or more glycerin derivative groups in one glycerin derivative-modified silicone molecule. Furthermore, the two or more glycerin derivative groups can be the same or different glycerin derivative groups. These two or more glycerin derivative groups may have a structure such that bonding occurs only in a side chain of polysiloxane, which is the main chain, only at a terminal of the polysiloxane, or in a side chain and at a terminal of the polysiloxane.

A glycerin derivative-modified silicone represented by general formula (1) and having a glycerin derivative group (-Q) is preferably liquid at least 100° C. Additionally, the polysiloxane main chain thereof may be any of a straight, branched, and reticulated (including fine crosslinked and elastomer forms). The manufacturing method of the present invention makes it possible to simply improve the opaque appearance of not only low-viscosity glycerin derivative-modified silicone, but also of glycerin derivative-modified silicone that is highly viscous to solid at room temperature (including rubbers with plasticity and poor fluidity), and to stabilize semi-opaque to transparent uniform liquids.

The particularly preferable glycerin derivative-modified silicone of the present invention is a glycerin derivative-modified silicone having a straight-chain polysiloxane structure represented by structural formula (1-1) below:

[Formula 34]

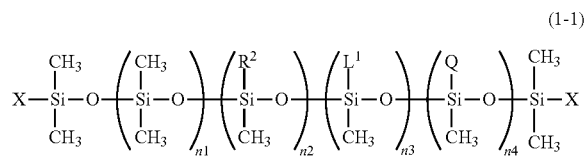
(1-1)

(wherein, $R^2$, $L^1$, and Q are each independently synonymous with those described above;
X is a group selected from the group consisting of a methyl group, $R^2$, $L^1$, and Q;
n1, n2, n3, and n4 are each independently a number in a range of 0 to 2,000, and n1+n2+n3+n4 is a number in a range of 0 to 2,000; however, when n4=0, at least one X is Q.)

In formula (1-1), (n1+n2+n3+n4) preferably is a number in a range of 10 to 2,000, more preferably is a number in a range of 25 to 1,500, and particularly preferably is a number in a range of 50 to 1,000. n1 preferably is a number in a range of 10 to 2,000, more preferably is a number in a range of 25 to 1,500, and particularly preferably is a number in a range of 50 to 1,000. n2 preferably is a number in a range of 0 to 250, more preferably is a number in a range of 0 to 150.

When $R^2$ is the long chain alkyl group, n2>1 is particularly preferable from the standpoint of compatibility with oil agents other than silicone and surface activity. n3 preferably is a number in a range of 0 to 250, and it is particularly preferable that it satisfies 3>1, and that there is at least one silylalkyl group (-$L^1$) having a siloxane dendron structure at

[Formula 36]

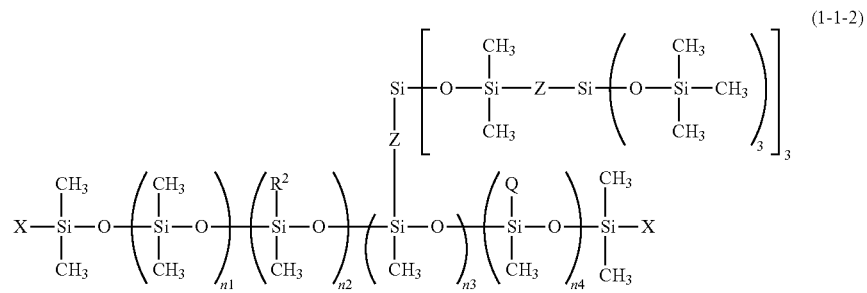

a side chain portion.[1]) n4 is a number in a range of 0 to 100, and preferably is a number in a range of 0 to 50. However, when n4=0, at least one X needs to be Q.

In the above structural formula (1-1), it is preferable that Q each independently is a glycerin derivative group represented by any of the above general formula (4-1) to general formula (4-4), and in the glycerin derivative-modified silicone, Q may all be one type of glycerin derivative group represented by any of the above general formula (4-1) to general formula (4-4), or some of Q in one molecule may be a glycerin derivative group represented by any of the above general formula (4-1) to general formula (4-4) and the remaining Q may be a different glycerin derivative group.

Furthermore, the glycerin derivative-modified silicone can be a mixture of at least one or two types of a glycerin derivative-modified silicone represented by general formula (1). More specifically, the glycerin derivative-modified silicone can be a mixture of at least two types of glycerin derivative-modified silicone, with different types of modified groups, modification rate, and degree of polymerization of the siloxane main chain.

As the glycerin derivative-modified silicone, the glycerin derivative-modified silicone represented by the following structural formula (1-1-1) is preferable:

[Formula 35]

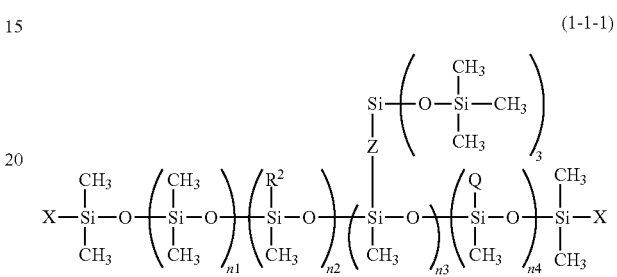

(wherein, $R^2$, Q, X, Z, n1, n2, n3, and n4 are synonymous with those described above), or the following structural formula (1-1-2):

(wherein, $R^2$, Q, X, Z, n1, n2, n3, and n4 are synonymous with those described above).

The modification rate of organopolysiloxane due to the glycerin derivative group is preferably in a range of 0.001 to 50 mol %, more preferably in a range of 0.01 to 30 mol %, and even more preferably in a range of 0.1 to 10 mol % of all functional groups bonded to polysiloxane, which is the main chain. Furthermore, in the glycerin derivative-modified silicone represented by structural formula (1-1), the modification rate (mol %) due to the glycerin derivative group is represented by the following formula:

Modification rate (mol %)=(number of glycerin derivative groups bonded to silicon atoms per molecule)/(6+2×(n1+n2+n3+n4))×100

For example, in the case of a glycerin derivative-modified silicone comprising trisiloxane having one glycerin derivative group, of the 8 silicon atom bonded functional groups, one is modified with the glycerin derivative group, so the modification rate by the glycerin derivative group is 12.5 mol %.

(Manufacturing Glycerin Derivative-Modified Silicone)

The glycerin derivative-modified silicone can be obtained by, for example, reacting (a1) a glycerin derivative having one reactive unsaturated group per molecule, (b1) organopolysiloxane having silicon atom bonded hydrogen atoms, and (c1) an organic compound having one reactive unsaturated group per molecule, and if necessary, (d1) a siloxane dendron compound having one reactive unsaturated group per molecule, and/or (e1) a long chain hydrocarbon compound or a chain organopolysiloxane compound having one reactive unsaturated group per molecule in the presence of a hydrosilylation reaction catalyst. The reactive unsaturated group preferably is an unsaturated functional group having a carbon-carbon double bond, and is exemplified by an alkenyl group or unsaturated fatty acid ester group. The —$R^1$ is introduced by component (c1), the -$L^1$ is introduced by component (d1), and the —$R^2$ is introduced by component (e1).

More specifically, a glycerin derivative-modified silicone can be obtained as below, for example.

The glycerin derivative-modified silicone can be obtained by addition-reacting an unsaturated organic compound having a carbon-carbon double bond at one terminal of the molecular chain and the monoalkenyl-containing glycerin derivative of the present invention with organopolysiloxane having a silicon-hydrogen bond. Furthermore, a siloxane dendron compound having a carbon-carbon double bond at one terminal of the molecular chain, and/or an unsaturated long chain hydrocarbon compound having a carbon-carbon double bond at one terminal of the molecular chain, or a chain organopolysiloxane having a carbon-carbon double bond at one terminal of the molecular chain may be further addition-reacted.

In the above case, the glycerin derivative-modified silicone can be obtained as the product of a hydrosilylation reaction between the unsaturated organic compound and the monoalkenyl-containing glycerin derivative of the present invention, and, optionally, the siloxane dendron compound and/or an unsaturated long chain hydrocarbon compound or a chain organopolysiloxane having a carbon-carbon double bond at one terminal of the molecular chain, and a SiH group-containing siloxane. This enables the introduction of an organic group and a glycerin derivative group, and optionally a silylalkyl group having a siloxane dendron structure and/or a long chain hydrocarbon group or a chain organopolysiloxane group into the polysiloxane chain of the glycerin derivative-modified silicone. This reaction can be performed as a batch or can take the form of successive reactions. However, successive reactions are preferable from the perspectives of safety and quality control.

For example, the glycerin derivative-modified silicone can be obtained by reacting at least (b2) organohydrogensiloxane represented by the following formula (1'):

[Formula 37]

(wherein $R^1$, a, b, c, and d are as described above), and (a2) monoalkenyl-containing glycerin derivative of the present invention, in the presence of a hydrosilylation reaction catalyst. It is preferable to further react (d) a siloxane dendron compound having one reactive unsaturated group per molecule, and/or (e) a hydrocarbon compound having one reactive unsaturated group per molecule, or chain organopolysiloxane having one reactive unsaturated group per molecule.

The glycerin derivative-modified silicone can be appropriately manufactured by, in a state where (a2) the monoalkenyl-containing glycerin derivative of the present invention and, optionally, (d) a siloxane dendron compound having one reactive unsaturated group per molecule and/or (e) a hydrocarbon compound having one reactive unsaturated group per molecule or a chain organopolysiloxane having one reactive unsaturated group per molecule, causing the constituent (a2), the constituent (d) and/or the constituent (e), and (b2) an organohydrogensiloxane represented by the above general formula (1') to react together, or alternatively sequentially addition-reacting the (b2) organohydrogensiloxane and, optionally, the constituent (d) and/or the constituent (e), and then further addition-reacting the constituent (a2).

As (b2) an organohydrogensiloxane used in the synthesis of the glycerin derivative-modified silicone, the organohydrogensiloxane is preferably represented by, for example, the following structural formula (1-1)':

[Formula 38]

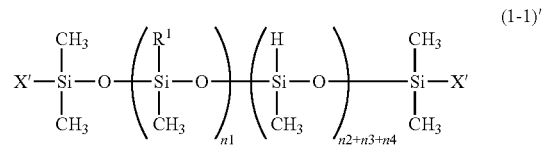

(wherein, $R^1$ are each independently synonymous with that described above;
X' is a group selected from $R^1$ or hydrogen atom; and
n1, n2, n3, and n4 are synonymous with those described above; however, when n2+n3+n4=0, at least one X' is a hydrogen atom)

The glycerin derivative-modified silicone is synthesized by causing a hydrosilylation reaction between (a) the monoalkenyl-containing glycerin derivative of the present invention and (b) an organohydrogenpolysiloxane, at that time, it is preferable that the organohydrogenpolysiloxane that is constituent (b) is an organohydrogensiloxane that is obtained by reacting the constituent (d1) and/or the constituent (e1) in addition reaction. In this case, the organohydrogensiloxane immediately prior to reaction with component (a) (after successive reactions with other components) is preferably represented by the following structural formula (1-1A).

[Formula 39]

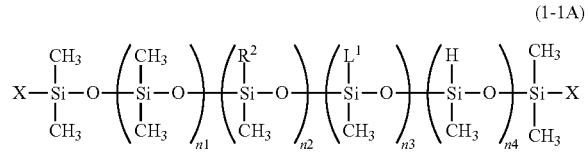

(wherein $R^2$ and $L^1$ are each independently synonymous with those described above;
X is selected from the groups comprising a methyl group, $R^2$, $L^1$, and a hydrogen atom (H); n1, n2, n3, and n4 are each independently a number in a range of 0 to 2,000, and n1+n2+n3+n4 is a number in a range of 0 to 2,000; however, when n4=0, at least one X is a hydrogen atom.)

In the glycerin derivative-modified silicone of the present invention, from the viewpoints of the thickening effect and gelation properties on oil ingredients, and use as a surfactant (emulsifier), and various treatment agents (powder dispersant or surface treatment agent), and use as a cosmetic raw material, the constituent (a) specifically is a monoalkenyl-containing glycerin derivative, which is a (poly)glycerin monoallyl ether or (poly)glycerin eugenol, and which has a monoglycerin, diglycerin, triglycerin, or tetraglycerin structure.

A glycerin derivative having an alkenyl group at the terminal of a molecular chain represented by structural formulae (4-1') to (4-4') below is an example of this constituent (a). In the formulae, $X^1$, $X^2$, and $R^{10}$ are groups synonymous with the groups described above, and m and q are numbers synonymous with the numbers described above. R' is an alkenyl group having a carbon-carbon double bond at the terminal, and preferably is a substituted or unsubstituted, straight or branched alkenyl group having from 3 to 5 carbon atoms. R' is preferably an allyl group.

[Formula 40]

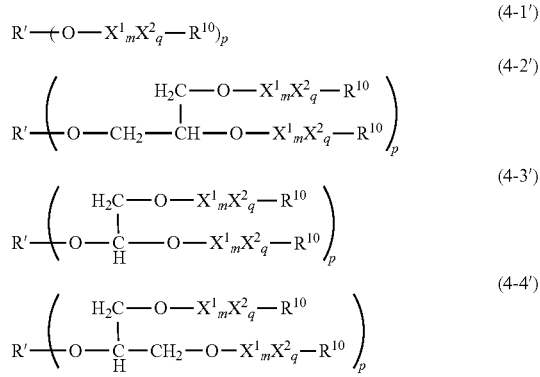

(d) The siloxane dendron compound that has one reactive unsaturated group per molecule used in the synthesis of the glycerin derivative-modified silicone of the present invention, is preferably a compound having a siloxane dendron structure with one carbon-carbon double bond at a molecular terminal, and is represented by the following general formula (3'):

[Formula 41]

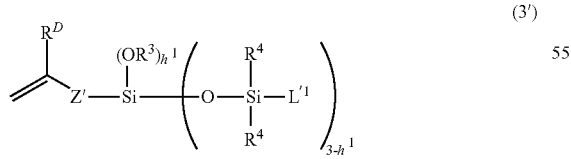

(In this formula,
$R^3$ and $R^4$ are synonymous with those described above, $R^D$ is a hydrogen atom or a methyl group;
Z' is a divalent organic group;
$h^1$ is a number in a range of 0 to 3;
$L'^1$ is the $R^4$ moiety or, when j=1, a silylalkyl group represented by general formula (3") below:

[Formula 42]

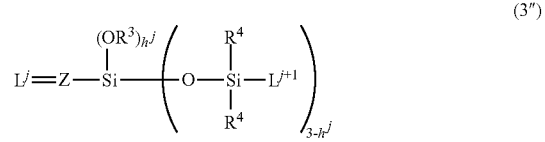

(wherein $R^3$ and $R^4$ are synonymous with those described above;
Z is a divalent organic group;
j indicates the number of generations of the silylalkyl group that is represented by $L^j$, when the number of generations (the number of repetitions) of the silylalkyl group is k', j is an integer of 1 to k', and the number of generations k' is an integer from 1 to 9; $L^{j+1}$ is the silylalkyl group when j is less than k' and is the $R^4$ moiety when j=k'; and
$h^j$ is a number in a range of 0 to 3)).

(e) The hydrocarbon compound having one reactive unsaturated group per molecule or chain organopolysiloxane having one reactive unsaturated group per molecule used in the synthesis of a glycerin derivative-modified silicone of the present invention, is preferably a mono unsaturated organic compound represented by the following general formula (2'):

[Formula 43]

(wherein R' is synonymous with that described above; and $R^{2'}$ represents a substituted or unsubstituted, straight or branched monovalent hydrocarbon group having 7 to 58 carbon atoms); or the following general formula (2-1):

[Formula 44]

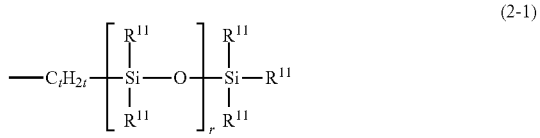

(wherein $R^{11}$, t, and r are synonymous with those described above); or the following general formula (2-2):

[Formula 45]

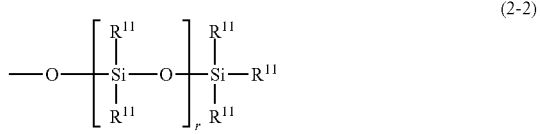

(wherein $R^{11}$ and r are synonymous with those described above).

The constituent (e) hydrocarbon compound having one reactive unsaturated group per molecule is preferably a monounsaturated hydrocarbon having from 9 to 30 carbon atoms and is more preferably a 1-alkene. Examples of the 1-alkene include 1-nonene, 1-decene, 1-undecene, 1-dodecene, 1-tridecene, 1-tetradecene, 1-hexadecene, 1-octadecene and the like. Examples of the chain organopolysiloxane having one reactive unsaturated group per molecule include a dimethylpolysiloxane capped at one molecular terminal with a vinyl group, a methylphenylpolysiloxane capped at one molecular terminal with a vinyl group, and the like.

The hydrosylilation reaction to synthesize glycerin derivative-modified silicone can be performed according to a known method in the presence or absence of a catalyst. Examples of the reaction solvent here include alcohol solvents, such as ethanol and isopropyl alcohol; aromatic hydrocarbon solvents, such as toluene and xylene; ether solvents, such as dioxane and THF; ester solvents, such as cetyl octanoate and isononyl isononanate; aliphatic hydrocarbon solvents, such as n-hexane, cyclohexane, n-heptane, cycloheptane, and methylcyclohexane; chlorinated hydrocarbon-based organic solvents, such as carbon tetrachloride; and silicone-based solvents, such as polydimethylsiloxane, hexamethyldisiloxane, methyltris-(trimethylsiloxane)silane, octamethyltetracyclosiloxane, decamethylpentacyclosiloxane, and octylheptamethyltrisiloxane.

The hydrosilylation reaction may be performed in the presence or absence of a catalyst, but preferably is performed in the presence of a catalyst because the reaction can be carried out at a low temperature and in a shorter period of time. Examples of the catalyst include platinum, ruthenium, rhodium, palladium, osmium, iridium, and similar compounds, and platinum compounds are particularly effective due to their high catalytic activity. Examples of the platinum compound include chloroplatinic acid; platinum metal; platinum metal supported on a carrier such as platinum supported on alumina, platinum supported on silica, platinum supported on carbon black, or the like; and a platinum complex such as platinum-vinylsiloxane complex, platinum-phosphine complex, platinum-phosphite complex, platinum alcoholate catalyst, or the like. When a platinum catalyst is used, the usage quantity of the solvent is approximately 0.0001 to 0.1 wt. %, and preferably 0.0005 to 0.05 wt. %, relative to the weight of the metal catalyst, but is not particularly limited.

A reaction temperature of the hydrosilylation reaction is typically from 30 to 120° C., and a reaction time is typically from 10 minutes to 24 hours and preferably from 1 to 10 hours.

When performing the above hydrosilylation reaction, it is preferable that the ratio of (the mass of carbon-carbon double bonds in the monoalkenyl-containing glycerin derivative of the present invention to the mass of silicon-bonded hydrogen atoms in the organohydrogenpolysiloxane to be added to the carbon-carbon double bonds in the glycerin derivative) is preferably in a range of 0.8 to 1.5, more preferably in a range of 1.0 to 1.3. Namely, when synthesizing the glycerin derivative-modified silicone of the present invention, it is more preferable to use a slight excess of the monoalkenyl-containing glycerin derivative of the present invention. Although processing with the ratio above 1.5 is also possible, the proportion of residual raw material increases, so it is not economical. Furthermore, when the ratio is in a range of 0.8 to 1.0, the amount of the silicon-bonded hydrogen atoms consumed by the hydrosilylation reaction falls into the range from 0.8 to 1.0, and silicon-bonded hydrogen atoms remain at the ratio of 0 to 0.2. However, it is possible to cause dehydrogenation reactions with hydroxyl groups contained in the glycerin derivative group and alcoholic hydroxyl groups of the reaction solvent, which can consume the remaining silicon-bonded hydrogen atoms, depending on the reaction conditions.

On the other hand, when the ratio is less than 0.8, there is a risk that unreacted organohydrogenpolysiloxane will remain. When such a glycerin derivative-modified silicone is used as the raw material for an external use preparation or a cosmetic composition, remaining organohydrogenpolysiloxane might react with the other raw materials, and generate hydrogen gas. This might cause such undesirable effects as alteration of the external use preparation or the cosmetic composition at the incorporation destination, fire, container expansion, and the like. In addition, when an attempt is made to consume the remaining silicon-bonded hydrogen atoms by using a dehydrogenation reaction when the ratio is less than 0.8, the proportion of Si—O—C crosslinked bonds increases, which increases the tendency to cause gelation during production. Therefore, it is preferable that the above ratio exceeds 0.8, i.e., that the reaction be performed under conditions in which there are more than 0.8 equivalents of the monoalkenyl-containing glycerin derivative of the present invention, so that the organohydrogenoplysiloxane is safely and completely consumed.

A third aspect of the present invention is an external use preparation, a cosmetic composition, or an industrial material that contains a glycerin derivative-modified silicone obtained by the manufacturing method of the present invention.

<External Use Preparation, Cosmetic Composition>

High-purity glycerin derivative-modified silicone obtained by the manufacturing method of the present invention can be appropriately blended into an external use preparation or cosmetic composition, and can constitute the external use preparation or cosmetic composition of the present invention. Additionally, raw materials for external use preparations and cosmetic compositions that contain high-purity glycerin derivative-modified silicone obtained by the manufacturing method of the present invention can be manufactured and can be blended into external use preparations and cosmetic compositions.

Specifically, high-purity glycerin derivative-modified silicone obtained by the manufacturing method of the present invention does not have a peculiar odor, and leaves virtually no odor during formulation or with the passage of time. There is an advantage in that there is virtually no cleavage of the silicon-oxygen bonds that may constitute the main chain of the glycerin derivative-modified silicone or the carbon-oxygen bonds that may constitute side chains. Therefore, high-purity glycerin derivative-modified silicone obtained by the manufacturing method of the present invention can be appropriately utilized as raw materials for external use preparations and cosmetic compositions used on the human body.

The high-purity glycerin derivative-modified silicone can be diluted with an appropriate medium, such as silicone oil, organic oil, or alcohols, and used as raw material for external use preparations and cosmetic compositions. The proportion of the high-purity glycerin derivative-modified silicone contained in raw material for use in external use preparations and cosmetic compositions is, based on the total weight (mass) of raw material, preferably 10 to 100 wt. (mass) %, more preferably 20 to 100 wt. (mass) %, and even more preferably 30 to 100 wt. (mass) %. The proportion of the high-purity glycerin derivative-modified silicone formulated into external use preparations and cosmetic compositions is not particularly limited, but, for example, based on the total weight (mass) of external use preparation or cosmetic composition, can be in a range of 0.1 to 40 wt. (mass) %, preferably 0.2 to 30 wt. (mass) %, more preferably 0.5 to 20 wt. (mass) %, and even more preferably 1 to 10 wt. (mass) %.

It is possible to employ high-purity glycerin derivative-modified silicone obtained by the manufacturing method of the present invention in applications common with those of the co-modified organopolysiloxanes described in Patent Document 6 (WO/2011/049248), Patent Document 7 (WO/2011/049247), and Patent Document 9 (Japanese Unexamined Patent Application Publication No. 2012-046507A), or the novel organopolysiloxane copolymer described in Patent Document 8 (WO/2011/049246) according to the structure thereof and the type of functional group possessed thereby. High-purity glycerin derivative-modified silicone obtained by the manufacturing method of the present invention can also be used in the same way as the co-modified organopolysiloxanes described in Patent Document 6, Patent Document 7, and Patent Document 9, and the novel organopolysiloxane described in Patent Document 8, in combination with any cosmetic raw material ingredients and in external use preparation, especially in forms, types and formulations of cosmetic preparations, and can be blended into various types of cosmetic compositions.

Specifically, glycerin derivative-modified silicone obtained by reactions with the high-purity monoalkenyl-containing glycerin derivative of the present invention, can exhibit excellent effects as emulsions, powder-in-oil dispersions, and surface-treated powder preparations for W/O. Furthermore, because the hydrophilic group therein does not have a molecular weight distribution that differs from conventional polyether groups, there is very little risk of fluctuations in quality and performance, allowing for a broader and more stable breadth of cosmetic formulation design. For example, with respect to the stability of oil dispersions of titanium oxide microparticles and zinc oxide microparticles, it was often the case, when low-performance powder dispersing agents, such as conventional polyether-modified silicone, were used, that agglutination would occur and the viscosity of the system would increase when titanium oxide microparticles and zinc oxide microparticles were used together in the same formulation. However, when glycerin derivative-modified silicone obtained by reacting the high-purity monoalkenyl-containing glycerin derivative of the present invention works as a dispersant for titanium oxide microparticles and zinc oxide microparticles, the formulation can be easily stabilized and made to have less viscosity, even in systems where they are used together.

The external use preparation of the present invention is not particularly limited, provided that it is a composition that is used on the human body as a cosmetic composition or medicine. Specific examples of cosmetic composition products of the present invention include skin cleansing agent products, skin care products, makeup products, anti-perspirant products, ultraviolet light blocking products, and similar skin use cosmetic products; hair use cleansing agent products, hair dressing products, hair use coloration products, hair growth products, hair rinsing products, hair conditioning products, hair treatment products, and similar hair use cosmetic products; and bath use cosmetic products. Examples of the medicament of the present invention include hair regrowth agents, hair growth promoters, analgesics, germicides, anti-inflammatory agents, refreshing agents, and skin anti-aging agents, but are not limited thereto.

The external use preparation is a product to be applied to human skin, nails, hair, and the like and, for example, medicament active components can be compounded therein and used in the treatment of various disorders. The cosmetic composition is also a product to be applied to human skin, nails, hair, and the like, and is used for beauty purposes. The external use preparation or cosmetic composition is preferably an anti-perspirant, a skin cleansing agent, a skin conditioner, a skin cosmetic composition product, a hair cleansing agent, an external use preparation for hair or a hair cosmetic composition.

An antiperspirant, a skin cleansing agent, a skin conditioner, a skin cosmetic composition product according to the present invention contains a high-purity glycerin derivative-modified silicone obtained by the manufacturing method of the present invention and the form thereof is not particularly limited, but may be any of a solution, emulsion, cream, solid, semisolid paste, gel, powder, laminate, mousse, or water-in-oil or oil-in-water emulsion composition (emulsion composition). Specific examples of the skin external use preparation or the skin cosmetic composition product according to the present invention include toilet water, emulsions, creams, sunscreen emulsions, sunscreen creams, hand creams, cleansing compositions, massage lotions, cleansing agents, antiperspirants, deodorants, and similar basic cosmetic products; foundations, make-up bases, blushers, rouges, eye shadows, eye liners, mascaras, nail enamels, and similar make-up cosmetic products; and the like.

Similarly, hair cleansing agents, hair external use preparations, and hair cosmetic compositions according to the present invention contain a high-purity glycerin derivative-modified silicone obtained by the manufacturing method of the present invention, and can be used in a variety of forms. For example, the hair cleansing agent, the hair external use preparation or the hair cosmetic composition product according to the present invention may be dissolved or dispersed in an alcohol, a hydrocarbon, a volatile cyclic silicone, or the like and used; furthermore, these may be used in the form of an emulsion by dispersing a desired emulsifier in water. Additionally, the hair cleansing agent, the hair external use preparation or the hair cosmetic composition product according to the present invention can be used as a spray by using propane, butane, trichloromonofluoromethane, dichlorodifluoromethane, dichlorotetrafluoroethane, carbonic acid gas, nitrogen gas, or a similar propellant. Examples of other forms include milk-like, cream-like, solid, semisolid paste-like, gel-like, powder-like, multilayer, mousse-like, and similar forms. These various forms can be used as shampooing agents, rinsing agents, conditioning agents, setting lotions, hair sprays, permanent wave agents, mousses, hair colorants, and the like.

The types, forms, and containers of cosmetic compositions or external use preparation compositions are common with those disclosed in paragraphs 0230 to 0233 of Patent Document 6.

The following other components generally used in external use preparations or cosmetic compositions may be added to the external use preparation or the cosmetic composition of the present invention, provided that such components do not inhibit the effectiveness of the present invention: water, powders or coloring agents, alcohols, water-soluble polymers, film-forming agents, oil agents, oil-soluble gelling agents, organo-modified clay minerals, surfactants, resins, UV absorbers, salts, moisturizing agents, preservatives, antimicrobial agents, perfumes, salts, antioxidants, pH adjusting agents, chelating agents, refreshing agents, anti-inflammatory agents, skin beautifying components (skin-lightening agents, cell activating agents, agents for ameliorating skin roughness, circulation promoters, astringents, antiseborrheic agents, and the like), vitamins, amino acids, nucleic acids, hormones, clathrates, and the like; bioactive substances, medicament active ingredients, and perfumes. However, the additives are not particularly limited to thereto.

Water that can be used in cosmetic compositions or external use preparations of the present invention is clean and does not contain ingredients that are harmful to the human body, examples of which include municipal water, purified water, mineral water, and deep-sea water.

(Oil Agent)

Oil agents that can be used in cosmetic composition or external use preparation of the present invention are at least one oil agent appropriately selected from silicone oils, nonpolar organic compounds or low-polarity to high-polarity organic compounds that are liquid at 5 to 100° C., and hydrocarbon oils, aliphatic ester oils, and liquid fatty acid triglycerides are preferable as nonpolar organic compounds or low-polarity to high-polarity organic compounds. These are components that are particularly widely used as base materials for cosmetic compositions, but it is possible to additionally use at least one or two types of compound selected from among known vegetable oils and fats, animal oils and fats, higher alcohols, fatty acid triglycerides, artificial sebum and fluorine-based oils as well as these oil agents.

By combining the hydrocarbon oil and/or the fatty acid ester oil with the silicone oil, in addition to the dry tactile sensation unique to silicone oils, moisture will be retained on the skin and a moisturizing feel whereby the skin or hair feels moisturized (also referred to as a luxurious tactile sensation) and smooth tactile sensation can be imparted to the cosmetic composition of the present invention. Moreover, there is a benefit in that stability over time of the cosmetic composition will not be negatively affected. Furthermore, with a cosmetic composition containing the hydrocarbon oil and/or the fatty acid ester oil and the silicone oil, these moisturizing components (the hydrocarbon oil and/or the fatty acid ester oil) can be applied on the skin or hair in a more stable and uniform manner. Therefore, the moisturizing effects of the moisturizing components on the skin are improved. Thus, compared to a cosmetic composition comprising only a non silicone-based oil agent (for example a hydrocarbon oil, a fatty acid ester oil, or the like), the cosmetic composition comprising a non silicone-based oil agent along with a silicone oil is advantageous in that a smoother, more luxurious tactile sensation is imparted.

These oil agents are common with those disclosed in paragraphs 0130 to 0135 and paragraph 0206 of Patent Document 6. Examples of the fluorine-based oil include perfluoropolyether, perfluorodecaline, perfluorooctane, and the like.

(Powders and Colorants)

Powders and colorants that can be used in the cosmetic composition or external use preparation of the present invention are generally used as cosmetic composition ingredients, and include white and colored pigments and extender pigments. The white and colored pigments are used to impart color and the like to the cosmetic composition, and the extender pigments are used to improve the tactile sensation and the like of the cosmetic composition. In the present invention, white and colored pigments as well as extender pigments commonly used in cosmetic compositions can be used as the powder without any particular restriction. In the present invention, preferably, at least one or two of the powders are compounded. The form (sphere, bar, needle, plate, amorphous, spindle, cocoon, or the like), particle size (aerosol, micro-particle, pigment-grade particle, or the like), and particle structure (porous, nonporous, or the like) of the powder are not limited in any way, but an average primary particle size is preferably in a range of 1 nm to 100 μm. Particularly, when compounding the powder or coloring agent as a pigment, preferably at least one or two selected from an inorganic pigment powder, an organic pigment powder, and a resin powder having an average particle size in a range of 1 nm to 20 μm is compounded.

Examples of the powder include inorganic powders, organic powders, surfactant metal salt powders (metallic soaps), colored pigments, pearl pigments, metal powder pigments, and the like. Compounded products of these pigments can be used. Furthermore, the surfaces of these pigments may be water-repellent treated.

These specific examples are common with the powders or colorants disclosed in paragraphs 0150 to 0152 of Patent Document 6.

Of the powders recited, description of a silicone elastomer powder will be given. The silicone elastomer powder is a crosslinked product of a straight-chain diorganopolysiloxane formed principally from diorganosiloxy units (D units), and can be preferably obtained by crosslinking an organohydrogenpolysiloxane having a silicon-bonded hydrogen atom on the side-chain or the molecular terminal and a diorganopolysiloxane having an unsaturated hydrocarbon group such as an alkenyl group or the like on the side-chain or the molecular terminal, in the presence of a hydrosilylation reaction catalyst. Compared to a silicone resin powder formed from T units and Q units, the silicone elastomer powder is soft, has elasticity, and has superior oil absorbency. Therefore, oils and fats on the skin can be absorbed and makeup smearing can be prevented. When surface treatment is thus performed with a high-purity glycerin derivative-modified silicone obtained by the manufacturing method of the present invention, because homogenous treatment is possible with good treatment efficiency, unique effect and tactile feel can be provided according to the type of said high-purity glycerin derivative-modified silicone, without the suede-like sensation of silicone elastomer powders. Furthermore, when the high-purity glycerin derivative-modified silicone is blended into a cosmetic composition together with a silicone elastomer powder, the dispersion stability of the powder in the cosmetic composition overall can be improved, and a cosmetic composition can be obtained that is stable over time.

The silicone elastomer powder can be in various forms such as spherical, flat, amorphous, or the like. The silicone elastomer powder may also be in the form of an oil dispersion. With the cosmetic composition of the present invention, the silicone elastomer powder is particulate in form, and the primary particle size observed using an electron microscope and/or the average primary particle size measured by laser analysis or scattering is in a range of 0.1 to 50 μm. Additionally, a silicone elastomer powder having spherical primary particles can be preferably compounded. The silicone elastomer that constitutes the silicone elastomer powder is preferably one having a hardness, as measured using a type A durometer in the "Rubber, Vulcanized or Thermoplastic—Determination of Hardness" specified in JIS K 6253, of 80 or less, and more preferably 65 or less.

Typical examples of this silicone elastomer powder, specifically silicone elastomer spherical powder, are common with that disclosed in paragraph 0168 of Patent Document 6, and may also be a silicone elastomer powder with various surface treatments, such as water repellent, as exemplified in paragraphs 0150 to 0152 of Patent Document 6.

It is possible to further blend another surfactant in the cosmetic composition or external use preparation of the present invention. These surfactants are cleansing components for skin or hair or components that function as emulsifiers for oil agents, and can be selected as appropriate according to the type and function of the cosmetic composition. More specifically, the other surfactants can be selected from the group consisting of an anionic surfactant, a cationic surfactant, a nonionic surfactant, an amphoteric surfactant, and a semipolar surfactant. Preferably a silicone-based nonionic surfactant is used in combination.

These surfactants are common with those disclosed in paragraphs 0162, 0163, and 0195 to 0201 of Patent Document 6. High-purity glycerin derivative-modified silicone obtained by the manufacturing method of the present invention has functionality as a dispersant when it has a polar group and a nonpolar group per molecule. Therefore, when combined with a nonionic surfactant, the diglycerin derivative-modified silicone functions as an aid to enhance the stability of the nonionic surfactant, and may improve the overall stability of the formulation. Specifically, because a high-purity glycerin derivative-modified silicone obtained by the manufacturing method of the present invention or a solution that contains a high-purity glycerin derivative-modified silicone has improved compatibility or affinity with various types of modified silicone, it can be used in combination with polyoxyalkylene-modified silicone, polyglycerin-modified silicone, glyceryl-modified silicone, sugar-modified silicone, and sugar alcohol-modified silicone, and such silicone-based nonionic surfactants can be appropriately used that have been alkyl branched, straight chain silicone branched, or siloxane dendrimer branched, and at the same time have a hydrophilic group, as necessary.

At least one or two types of polyhydric alcohol and/or monohydric lower alcohol can be used in the cosmetic composition or external use preparation of the present invention, according to the purpose thereof. These alcohols are common with those disclosed in paragraphs 0159 and 0160 of Patent Document 6.

At least one or two types of inorganic salt and/or organic salt can be used in the cosmetic composition or external use preparation of the present invention, according to the purpose thereof. These salts are common with those disclosed in paragraph 0161 of Patent Document 6.

At least one selected from the group consisting of cross-linked organopolysiloxane, organopolysiloxane elastomer spherical powder, silicone resin, acrylic silicon dendromer copolymer, silicone rubber, polyamide-modified silicone, alkyl-modified silicone wax, and alkyl-modified silicone resin wax can be used in the cosmetic composition or external use preparation of the present invention, according to the purpose thereof. These silicone-based ingredients are common with those disclosed in paragraphs 0162 to 0194 of Patent Document 6.

At least one or two types of water-soluble polymers can be used in the cosmetic composition or external use preparation of the present invention, according to the purpose thereof. These water-soluble polymers are common with those disclosed in paragraph 0201 of Patent Document 6.

At least one or two types of ultraviolet light blocking components can be used in the cosmetic composition or external use preparation of the present invention, according to the purpose thereof. These ultraviolet light blocking components are common with the organic and inorganic ultraviolet light blocking components disclosed in paragraphs 0202 to 0204 of Patent Document 6, but specifically they are at least one selected from the group consisting of titanium oxide microparticles, zinc oxide microparticles, 2-ethylhexyl para-methoxycinnamate, 4-tert-butyl-4'-methoxydibenzoyl methane, diethylaminohydroxybenzoyl hexyl hexylbenzoate, benzotriazol-based ultraviolet absorbents, and triazine-based ultraviolet absorbents, such as 2,4,6-tris-(4-(2-ethylhexyloxycarbonyl) anylino) 1,3,5-triazine [INCI: octyltriazone] and 2,4-bis-[(4-(2-ethyl-hexyloxy)-2-hydroxy)phenyl]-6-(4-methoxyphenyl)-1,3,5,triazine [INCI:bis-ethylhexyloxyphenol methoxyphenyl triazine, tradename: Chinosolve S (R)). These ultraviolet light blocking components are generally used, are easy to acquire, and have high ultraviolet light blocking effects and, thus can be beneficially used. In particular, using both inorganic and organic ultraviolet light blocking components is preferable, and using a UV-A blocking component in combination with a UV-B blocking component is more preferable.

By using the high-purity glycerin derivative-modified silicone and ultraviolet light blocking component in combination in the cosmetic composition or external use preparation of the present invention, the overall tactile feel and storage stability of a cosmetic composition are improved, while making it possible to stably disperse the ultraviolet light blocking components in the cosmetic composition, and therefore a cosmetic composition can be provided with excellent ultraviolet blocking function.

Various components other than the components described above can be used in the cosmetic composition or external use preparation of the present invention, provided that such use does not impair the effects of the present invention. Examples thereof include oil-soluble gelling agents, organo-modified clay minerals, preservatives, bioactive components, skin beautifying components, pH adjusting agents, antioxidants, solvents, chelating agents, moisturizing components, perfumes and the like. These elective cosmetics ingredients are common with those disclosed in paragraphs 0207, 0208, and 0220 to 0228 of Patent Document 6.

Additionally, when the external use preparation or the cosmetic composition according to the present invention is an anti-perspirant, or depending on the purpose thereof, the external use preparation or the cosmetic composition can contain an anti-perspiration active component and/or a deodorant agent. These antiperspirant ingredients and deodorant ingredients are common with those disclosed in paragraphs 0209 to 0219 of Patent Document 6. Similarly, when the cosmetic composition or external use preparation of the present invention is an antiperspirant composition, the methods of preparation and use of the various antiperspirant compositions are common with those disclosed in paragraphs 0234 to 0275 of Patent Document 6.

INDUSTRIAL APPLICABILITY

Specifically, the high-purity monoalkenyl-containing glycerin derivative of the present invention can be appropriately used as an organic modifier for use in the manufacture of glycerin derivative-modified silicone. Additionally, besides being appropriately usable as raw material for medical goods or cosmetic compositions, the glycerin derivative-modified silicone of the present invention can also be appropriately used as raw material for various industrial materials, for example, as a fiber treatment agent, a varnish or paint additive of excellent heat resistance, weather resistance, and electrical properties, a coating agent, a primer, an adhesive, foaming stabilizer, or modifier for various urethanes or polyol base compound for forming materials, a mold separation agent or release agent, an antifoaming agent, a grease or oil compound, an oil for insulation, glossing, water repelling, heat medium or coolant, or lubricant, a modifier, additive, or surface treatment agent for rubbers and resins, a surfactant, a formulation, modifier, or precursor for silane coupling agents, a coating material or sealing material for construction or lining uses, a protective agent, lubricant, or buffer for fiber optics or wires, and electronics and electrical components.

WORKING EXAMPLES

Hereinafter, the present invention is described in detail with reference to working examples and comparative examples, but it should be understood that the present invention is not limited to these working examples.

Furthermore, in the following, the GC purity and electrical conductivity were measured as described below.

(GC Purity)

0.1 g of sample and 10 cc of acetone were placed in a 20 cc vial, sealed with a stopper, and then shaken until uniformly mixed. The purity was then found by surface area using GC-2010, manufactured by Shimadzu Corp., equipped with a FID detector and DB-5 ms capillary column.

(Electrical Conductivity)

1.5 g of sample and 75 g of ion exchanged water with electrical conductivity of not greater than 2 μS/cm were placed in a 100 cc plastic bottle, sealed with a stopper, and thoroughly shaken to mix. The electrical conductivity was then measured using CM-30G EC Meter manufactured by DKK-Toa(Toa-denpa-kogyo) Corp. Specimen temperature was in a range of 20 to 25° C.

Working Example 1: <Monoallyl Diglycerin Synthesis>

628.6 g of 2,2-dimethyl-1,3-dioxolane-4-methanol (reagent manufactured by Wako Pure Chemical Industries Co.) and 18.0 g of 28% sodium methoxide methanol solution (reagent manufactured by Wako Pure Chemical Industries Co.) were placed in a reaction vessel in a nitrogen atmosphere, and thoroughly stirred and heated to 100° C. Next, 271.5 g of allyl glycidyl ether (NEOALLYL G manufactured by Daiso Co.) were then dripped over 5 hours into this solution. After dripping, the temperature was raised to 110° C., and heating and stirring was continued for one hour. After confirming by gas chromatography that the peak for allyl glycidyl ether had disappeared, 24.0 g of acetic acid was added and heated stirring was continued for 30 minutes. 402.0 g of a ketal of monoallyl diglycerin was then obtained by distillation at 145 to 154° C. and not greater than 5 mmHg. The product was a transparent pale yellow liquid with GC purity of 94%.

Furthermore, 350.2 g of the resulting ketal of monoallyl diglycerin, 0.36 g of strong hydrochloric acid, and 69.8 g of ion exchanged water were placed in another reaction vessel in a nitrogen atmosphere and heated to 80 to 90° C., while thoroughly stirring, after which, heating and stirring was continued for one hour. Acetone was produced during this time, but was removed by the nitrogen flow. Furthermore, residual acetone and excess water were removed by reducing pressure. The internal liquid pH at this time was 1. After restoring the pressure, 18.0 g of ion exchanged water was added and heated and stirred for 30 minutes, and then water and other low-boiling point components and acids were removed by reducing pressure. The internal liquid pH at this time was 3. Furthermore, after restoring the pressure, 17.9 g of ion exchanged water was added and heated and stirred for 30 minutes, and then heated under reduced pressure for 3 hours to remove other low-boiling point components and acids. The internal liquid pH at this time was 6. Filtering with Radiolite #900 (manufactured by Showa Chemical Industries Co.) yielded 240.0 g of monoallyl diglycerin. The product was a transparent yellow liquid with GC purity of 97% and electrical conductivity of 3.1 μS/cm.

Working Example 2: <Monoallyl Diglycerin Synthesis>

144.9 g of ketal of monoallyl diglycerin was obtained by performing synthesis in the same manner as in Working Example 1, using 286.0 g of 2,2-dimethyl-1,3-dioxolane-4-methanol (reagent manufactured by reagent manufactured by Wako Pure Chemical Industries Co.), 9.0 g of 28% sodium methoxide methanol solution (reagent manufactured by reagent manufactured by Wako Pure Chemical Industries Co.), and 164.7 g of allyl glycidyl ether (NEOALLYL G manufactured by Daiso Co.) as raw materials, and without using acetic acid. The product was a transparent pale yellow liquid. Next, 90.1 g of the resulting ketal of monoallyl diglycerin, 0.09 g of strong hydrochloric acid, and 9.0 g of ion exchanged water were combined, heated to 80 to 90° C., while stirring thoroughly, and heating and stirring was continued for one hour. Acetone was produced during this time, but was removed by the nitrogen flow. Furthermore, residual acetone and excess water were removed by reducing pressure. After restoring the pressure, 9.1 g of ion exchanged water was added and heated and stirred for 30 minutes, and then water and other low-boiling point components and acids were removed by reducing pressure. Furthermore, after restoring the pressure, 9.1 g of ion exchanged water was added and heated and stirred for 30 minutes, and then water and other low-boiling point components and acids were removed by heating and reducing pressure for 3 hours, thereby yielding 73.7 g of monoallyl diglycerin, without filtering. The pH of the product was 6. The product was a transparent yellow liquid with GC purity of 97% and electrical conductivity of 3.2 μS/cm.

Working Example 3: <Monoallyl Diglycerin Synthesis>

134.8 g of ketal of monoallyl glycerin was obtained by performing synthesis in the same manner as in Working Example 1, using 558.8 g of 2,2-dimethyl-1,3-dioxolane-4-methanol (reagent manufactured by Wako Pure Chemical Industries Co.), 3.4 g of sodium hydroxide (reagent manufactured by Wako Pure Chemical Industries Co.) instead of 28% sodium methoxide methanol solution, 241.30 g of allyl glycidyl ether (NEOALLYL G manufactured by Daiso Co.), and 5.3 g of acetic acid as raw materials. The appearance of the product was a transparent very pale yellow liquid with GC purity of 97%. Next, 301.0 g of the resulting ketal of monoallyl diglycerin, 0.3 g of strong hydrochloric acid, and 60.0 g of ion exchanged water were combined, heated to 80 to 90° C., while stirring thoroughly, and heating and stirring was continued for one hour. Acetone was produced during this time, but was removed by the nitrogen flow. Furthermore, residual acetone and excess water were removed by reducing pressure. After restoring the pressure, 15.2 g of ion exchanged water was added, and heated and stirred for 30 minutes, and then water and other low-boiling point components and acids were removed by reducing pressure. Furthermore, after restoring the pressure, 15.6 g of ion exchanged water was added, and heated and stirred for 30 minutes, and then heated under reduced pressure for 3 hours to remove other low-boiling point components and acids. Filtering with Radiolite #900 (manufactured by Showa Chemical Industries Co.) yielded 203.0 g of monoallyl diglycerin. The pH of the product was 6. The product was a transparent pale yellow liquid with GC purity of 96% and electrical conductivity of 2.2 µS/cm.

Working Example 4: <Monoallyl Diglycerin Synthesis>

148.7 g of glycerin (reagent manufactured by Wako Pure Chemical Industries Co.), 253.3 g of 2,2-dimethoxypropane (reagent manufactured by Wako Pure Chemical Industries Co.), and p-toluene sulfonic acid monohydrate (Wako Pure Chemical Industries) were placed in a reaction vessel, in a nitrogen atmosphere, and heated to 45° C. while stirring thoroughly. After one hour, after confirming by gas chromatography that glycerin had disappeared, the methanol that had been produced and excess raw ingredients were removed under reduced pressure to yield a 216.0 g mixture of 2,2-dimethyl-1,3-dioxolane-4-methyanol and p-toluene sulfonic acid.

133.0 g of ketal of monoallyl diglycerin was obtained by performing synthesis in the same manner as in Working Example 1, using 216.0 g of the resulting mixture of 2,2-dimethyl-1,3-dioxolane-4-methanol and p-toluene sulfonic acid, 13.6 g of 28% sodium methoxide methanol solution (reagent manufactured by Wako Pure Chemical Industries Co.), 124.6 g of allyl glycidyl ether (NEOALLYL G manufactured by Daiso Co.), and 4.2 g of acetic acid as raw materials. The appearance of product was a transparent colorless liquid with GC purity of 98%. Next, 30.4 g of the resulting ketal of monoallyl diglycerin, 0.006 g of sodium hydrogensulfate monohydrate (Kanto Kagaku Co.) instead of strong hydrochloric acid, and 5.1 g of ion exchanged water were combined, heated to 80 to 90° C., while stirring thoroughly, and heating and stirring was continued for one hour. Acetone was produced during this time, but was removed by the nitrogen flow. Furthermore, residual acetone and excess water were removed by reducing pressure. After restoring the pressure, 5.1 g of ion exchanged water was added, and heated and stirred for 30 minutes, and then water and other low-boiling point components and acids were removed by reducing pressure. Furthermore, after restoring the pressure, 5.0 g of ion exchanged water was added, and heated and stirred for 30 minutes, and then water and other low-boiling point components and acids were removed by heating and reducing pressure for 3 hours to yield 24.6 g of monoallyl diglycerin, without filtering. The product was a transparent colorless liquid with GC purity of 93% and electrical conductivity of 17.8 µS/cm.

Working Example 5: <Monoallyl Diglycerin Synthesis>

311.3 g of ketal of monoallyl diglycerin was obtained by performing synthesis in the same manner as in Working Example 1, using 558.7 g of 2,2-dimethyl-1,3-dioxolane-4-methanol (reagent manufactured by Wako Pure Chemical Industries Co.), 16.0 g of 28% sodium methoxide methanol solution (reagent manufactured by Wako Pure Chemical Industries Co.), 241.3 g of allyl glycidyl ether (reagent manufactured by Wako Pure Chemical Industries Co.), and 7.6 g of acetic acid as raw materials. The product was a transparent pale yellow liquid with GC purity of 98%. Next, 120.7 g of the resulting ketal of monoallyl diglycerin, 0.1 g of strong hydrochloric acid, and 23.9 g of ion exchanged water were combined, heated to 80 to 90° C., while stirring thoroughly, and heating and stirring was continued for one hour. Acetone was produced during this time, but was removed by the nitrogen flow. Furthermore, residual acetone and excess water were removed by reducing pressure. After restoring the pressure, 6.5 g of ion exchanged water was added, and heated and stirred for 30 minutes, and then water and other low-boiling point components and acids were removed by reducing pressure. Furthermore, after restoring the pressure, an aqueous solution obtained from 0.1 g of sodium bicarbonate and 7.97 g of ion exchanged water was added, and heated and stirred for 30 minutes, and then water and other low-boiling point components and acids were removed by heating and reducing pressure for 3 hours. Filtering with Radiolite #900 (manufactured by Showa Chemical Industries Co.) yielded 72.2 g of monoallyl diglycerin. The pH of the product was 7. The product was a transparent colorless liquid with GC purity of 97% and electrical conductivity of 28.4 µS/cm.

Comparative Example 1: <Monoallyl Diglycerin Synthesis>

558.8 g of 2,2-dimethyl-1,3-dioxolane-4-methanol (reagent manufactured by Wako Pure Chemical Industries Co.) and 16.0 g of triethylamine (reagent manufactured by Wako Pure Chemical Industries Co.) were placed in a reaction vessel in a nitrogen atmosphere and heated to 80° C. while stirring thoroughly. Next 241.3 g of allyl glycidyl ether (NEOALLYL G manufactured by Daiso Co.) was dripped into this solution over 5 hours. After dripping, the temperature was raised to 100° C. and heating and stirring was continued for one hour. After confirming by gas chromatography that the peak for allyl glycidyl ether had disappeared, 365.2 g of ketal of monoallyl diglycerin was obtained by distillation at 145 to 154° C. and not greater than 5 mmHg. The product was a transparent pale yellow liquid with GC purity of 93%. Peaks not seen for Working Examples 1 to 5 were seen in the GC chart.

Furthermore, 320.0 g of the resulting ketal of monoallyl diglycerin, 0.32 g of strong hydrochloric acid, and 65.8 g of ion exchanged water were placed in another reaction vessel in a nitrogen atmosphere and heated to 80° C., while thoroughly stirring. Because the pH was 9, 2.86 g of strong hydrochloric acid was added to reduce the pH to 4, at which time acetone began to be produced. After continuing heating and stirring for one hour in this state, residual acetone and excess water were removed by reducing pressure. After restoring the pressure, 16.6 g of ion exchanged water was added and heated and stirred for 30 minutes, and then water and other low-boiling point components and acids were removed. Furthermore, 16.5 g of ion exchanged water was added and heated and stirred for 30 minutes, and then water and other low-boiling point components and acids were removed by heating and reducing pressure for 3 hours to yield 268.5 g of monoallyl diglycerin. The product was a transparent pale yellow liquid with GC purity of 91% and electrical conductivity of 179.4 µS/cm. Peaks not seen for Working Examples 1 to 5 were confirmed in the GC chart.

Comparative Example 2: <Monoallyl Diglycerin Synthesis>

279.5 g of 2,2-dimethyl-1,3-dioxolane-4-methanol (reagent manufactured by Wako Pure Chemical Industries Co.) and 1.8 g of tetramethyl-1,3-diaminopropane (Tokyo Chemical Industry Co.) were placed in a reaction vessel in a nitrogen atmosphere and heated to 80° C. while stirring thoroughly. Next 120.1 g of allyl glycidyl ether (NEOALLYL G manufactured by Daiso Co.) was dripped into this solution over 5 hours. After dripping, the temperature was raised to 100° C. and heating and stirring was continued for one hour. After confirming by gas chromatography that the peak for allyl glycidyl ether had disappeared, residual raw materials and low-boiling point components were removed at 110° C. and not greater than 5 mmHg. Next, after cooling to room temperature, liquid extraction was performed with 1300 g of ion exchanged water to remove the water-insoluble constituents that exhibited dark colors. Water was removed from the resulting aqueous solution by reducing pressure under conditions of 90° C. and not greater than 5 mmHg to yield 178.5 g of ketal of monoallyl diglycerin. The product was a transparent orange liquid.

Furthermore, 100.0 g of the resulting ketal of monoallyl diglycerin, 5.5 g of strong hydrochloric acid, and 16.0 g of ion exchanged water were placed in another reaction vessel in a nitrogen atmosphere and heated to 80° C., while thoroughly stirring. Acetone was produced during this time, but was removed by the nitrogen flow. Furthermore, residual acetone and excess water were removed by reducing pressure. After continuing heating and stirring for one hour in this state, residual acetone and excess water were removed by reducing pressure. After restoring the pressure, 10.0 g of ion exchanged water was added, and heated and stirred for 30 minutes, after which, water and other low-boiling point components and acids were removed for 3 hours by heating and reducing pressure, and then adsorption treatment with 1.5 g of KYOWAAD 500SN (manufactured by Kyowa Chemical Industry Co.) and filtering with Radiolite #900 yielded 60.6 g of monoallyl diglycerin. The pH was 7. The product was a transparent orange liquid with electrical conductivity of 94.3 µS/cm.

The results for Working Examples 1 to 5 and Comparative Examples 1 and 2 are shown in Table 1.

TABLE 1

|  | Working Example 1 | Working Example 2 | Working Example 3 | Working Example 4 |
|---|---|---|---|---|
| Catalyst in ketal synthesis | NaOMe | NaOMe | NaOH | NaOMe |
| Ketal purification method | Distillation | Distillation (not neutralized) | Distillation | Distillation |
| Catalyst in synthesis of monoalkenyl-containing glycerin derivative | Hydrochloric acid | Hydrochloric acid | Hydrochloric acid | Sodium hydrogensulfate monohydrate (small amount) |
| Acid removal method | Reduced pressure removal | Reduced pressure removal | Reduced pressure removal | Removal N/A |
| GC purity | 97% | 97% | 96% | 93% |
| electrical conductivity | 3.1 µS/cm | 3.2 µS/cm | 3.2 µS/cm | 17.8 µS/cm |

|  | Working Example 5 | Comparative Example 1 | Comparative Example 2 |
|---|---|---|---|
| Catalyst in ketal synthesis | NaOMe | Et$_3$N | *1 |
| Ketal purification method | Distillation | Distillation | Aqueous layer extraction |
| Catalyst in synthesis of monoalkenyl-containing glycerin derivative | Hydrochloric acid | Hydrochloric acid | Hydrochloric acid |
| Acid removal method | Neutralized with sodium hydrogen carbonate | Reduced pressure removal | Reduced pressure removal |
| GC purity | 97% | 91% | — |
| electrical conductivity | 28.4 µS/cm | 179.4 µS/cm | 94.3 µS/cm |

*1 tetramethyl-1,3-diaminopropane

Working Example 6: <Modified Silicone Synthesis>

In the compositional formulae below, Me represents a methyl (—CH$_3$) group, a Me$_3$SiO group (or a Me$_3$Si group) is represented by "M", a Me$_2$SiO group is represented by "D", a MeHSiO group is represented by "D$^H$", and units in which methyl groups in M and D are modified with a substituent group are represented by "M$^R$" and "D$^R$". Additionally, in the production examples, "IPA" represents isopropyl alcohol.

Step 1: 215.0 g of methylhydrogen polysiloxane represented by the average composition formula MD$_{47.5}$D$^H_{10.5}$M and 17.0 g of vinyl tris-trimethylsiloxy silane represented by the average composition formula CH$_2$=CH—Si(OSiMe$_3$)$_3$ were placed in a reaction vessel, and 0.39 g of a hexamethyl disiloxane solution of platinum-1,3-divinyl-1,1,3,3-tetramethyl disiloxane complex was added while stirring at 25° C. under a nitrogen flow (Pt concentration 0.4 wt. %). The reaction liquid was heated to 65 to 75° C. and allowed to react for 4 hours. Then, 2 g of the reaction liquid was sampled and it was confirmed that the reaction rate was not in error through an alkali decomposition gas generation method.

Step 2: Heat generated upon adding 47.2 g (first adding) of hexadecene (α-olefin purity=91.7%) raised the temperature from 39° C. to 68° C. It was confirmed that the target reaction rate had been achieved by the same alkali decomposition gas generation method as in step 1.

Step 3: 23.7 g of the monoallyl diglycerin obtained in Working Example 1, 0.035 g of natural vitamin E, and 245 g of IPA were added to the reaction liquid, and then an additional 0.39 g of the same platinum catalyst solution as above was infused. When reacted for 4 hours at 45 to 65° C., it was confirmed that the target reaction rate had been achieved by the same method as in step 1.

Step 4: 47.2 g of hexadecene (second adding) and an additional 0.2 g of the same platinum catalyst solution as above were added to the reaction liquid and reacted for 6 hours at 60 to 70° C. The reaction was completed upon confirmation by the same method as in step 1.

Step 5: IPA was distilled out under reduced pressure at 70 to 80° C., and stripping was further performed for 3 hours under conditions of 95 to 105° C. and 10 Torr to distill out low-boiling point components.

Step 6: 5.3 g of an aqueous solution of 0.16% sodium hydrogensulfate monohydrate was added to the contents of the reaction vessel and acid treatment was performed for 30 minutes at 60 to 70° C. while stirring under a nitrogen flow. Water and low-boiling point components were then stripped under conditions of 10 Torr. Furthermore, 3 g of ion exchanged water was added and twice acid treatment was performed for 30 minutes and water and low-boiling point components were stripped under conditions of 10 Torr. Finally, stripping was performed for 3 hours under conditions of 60 to 70° C. and 10 Torr to distill out water and low-boiling point components. Furthermore, filtering yielded 270 g of a composition containing diglycerin derivative-modified silicone represented by the average composition formula $MD_{47.5}D^{R*11}_{7.5}D^{R*31}_{1}D^{R*22}_{2}M$ in the form of a uniform, opaque pale brown liquid. Viscosity was 8400 mPa s.

In this formula, $R^{*11}$=—$C_{16}H_{33}$.
$R^{*31}$=—$C_2H_4Si(OSiMe_3)_3$
$R^{*22}$ is represented by —$C_3H_6O$—X, where "X" is the diglycerin portion.

Working Example 7: <Modified Silicone Synthesis>

Step 1: 113.2 g of methylhydrogen polysiloxane represented by the average composition formula $MD_{26}D^H_{10}M$ and 27.5 g of vinyl tris-trimethylsiloxy silane represented by the average composition formula $CH_2$=CH—$Si(OSiMe_3)_3$ were placed in a reaction vessel, and 0.13 g of a hexamethyl disiloxane solution of platinum-1,3-divinyl-1,1,3,3-tetramethyl disiloxane complex (Pt concentration 0.4 wt. %) was added while stirring under a nitrogen flow at 25° C. The reaction liquid was heated to 65 to 75° C. and allowed to react for 4 hours. Then, 2 g of the reaction liquid was sampled and it was confirmed that the reaction rate was not in error through an alkali decomposition gas generation method.

Step 2: Heat was generated in the reaction liquid when 25.1 g (first adding) of dodecene (α-olefin purity=95.4%) was added. 2 g of the reaction liquid was sampled and it was confirmed that the target reaction rate had been achieved by the same alkali decomposition gas generation method as in step 1.

Step 3: 9.22 g of the monoallyl diglycerin obtained in Working Example 1 and 40 g of toluene were added to the reaction liquid, and then an additional 0.10 g of the same platinum catalyst solution as above was infused. When reacted for 4 hours at 45 to 65° C., it was confirmed that the target reaction rate had been achieved by the same method as in step 1.

Step 4: 25.1 g of dodecene (second adding) and an additional 0.06 g of the same platinum catalyst solution as above were added to the reaction liquid and reacted for 6 hours at 60 to 70° C. The reaction was completed upon confirmation by the same method as in step 1.

Step 5: Toluene was distilled out under reduced pressure at 70 to 140° C., and stripping was further performed for 3 hours under conditions of 140° C. and 10 Torr to distill out low-boiling point components.

Step 6: 1.5 g of an aqueous solution of 1% sodium hydrogensulfate monohydrate was added to the contents of the reaction vessel and acid treatment was performed for 30 minutes at 60 to 70° C. while stirring under a nitrogen flow. Water and low-boiling point components were then stripped under conditions of 10 Torr. Furthermore, 1.5 g of ion exchanged water was added and twice acid treatment was performed for 30 minutes and water and low-boiling point components were stripped under conditions of 10 Torr. Finally, stripping was performed for 1 hour under conditions of 60 to 70° C. and 10 Torr to distill out water and low-boiling point components. Furthermore, filtering yielded 140 g of a composition containing diglycerin derivative-modified silicone represented by the average composition formula $MD_{26}D^{R*11}_{7}D^{R*11}_{2}D^{R*22}_{1}M$ in the form of a uniform, opaque pale brown liquid.

In this formula, $R^{*11}$=—$C_{12}H_{25}$.
$R^{*31}$=—$C_2H_4Si(OSiMe_3)_3$
$R^{*22}$ is represented by —$C_3H_6O$—X, where "X" is the diglycerin portion.

Comparative Example 3: <Modified Silicone Synthesis>

Step 1: 122.9 g of methylhydrogen polysiloxane represented by the average composition formula $MD_{47.5}D^H_{10.5}M$ and 9.7 g of vinyl tris-trimethylsiloxy silane represented by the average composition formula $CH_2$=CH—$Si(OSiMe_3)_3$ were placed in a reaction vessel, and 0.2 g of a hexamethyl disiloxane solution of platinum-1,3-divinyl-1,1,3,3-tetramethyl disiloxane complex (Pt concentration 0.4 wt. %) was added while stirring under a nitrogen flow at 25° C. The reaction liquid was heated to 65 to 75° C. and allowed to react for 4 hours. Then, 2 g of the reaction liquid was sampled and it was confirmed that the reaction rate was not in error through an alkali decomposition gas generation method.

Step 2: 27.0 g of hexadecene (α olefin purity=91.7%) was added to the reaction liquid (first adding) and the heat generated thereby caused the temperature to rise from 34° C. to 55° C. It was confirmed that the target reaction rate had been achieved by the same alkali decomposition gas generation method as in step 1.

Step 3: 13.9 g of the monoallyl diglycerin obtained in Working Example 1, 0.2 g of natural vitamin E, and 140.0 g of IPA were added to the reaction liquid, and then an additional 0.02 g of the same platinum catalyst solution as above was infused. When reacted for 4 hours at 45 to 65° C., it was confirmed that the target reaction rate had been achieved by the same method as in step 1.

Step 4: 27.0 g of hexadecene (second adding) and an additional 0.2 g of the same platinum catalyst solution as above were added to the reaction liquid and reacted for 6 hours at 60 to 70° C. The reaction was completed upon confirmation by the same method as in step 1.

Step 5: IPA was distilled out under reduced pressure at 70 to 80° C., and stripping was further performed under conditions of 95 to 105° C. and 10 Torr to distill out low-boiling point components.

Step 6: 3.0 g of an aqueous solution of 0.16% sodium hydrogensulfate monohydrate was added to the contents of the reaction vessel and acid treatment was performed for 30 minutes at 60 to 70° C. while stirring under a nitrogen flow. Water and low-boiling point components were then stripped under conditions of 10 Torr. Furthermore, 3 g of ion exchanged water was added and twice acid treatment was performed for 30 minutes and water and low-boiling point components were stripped under conditions of 10 Torr. Finally, stripping was performed for 3 hours under conditions of 60 to 70° C. and 10 Torr to distill out water and low-boiling point components. Furthermore, filtering yielded 140 g of diglycerin derivative-modified silicone in the form of a semi-opaque pale brown liquid. Viscosity was low at 2630 mPa s. However, structural analysis by 13C NMR and 29Si NMR confirmed a Si—O—C bond in which the hydroxyl groups and SiH groups had reacted in the raw materials used. As shown in Comparative Examples 9 to 11, it was found that the water-in-oil emulsifying performance was actually insufficient.

Comparative Example 4: <Modified Silicone Synthesis>

Step 1: 215.4 g of methylhydrogen polysiloxane represented by the average composition formula $MD_{47.5}D^H{}_{10.5}M$ and 17.0 g of vinyl tris-trimethylsiloxy silane represented by the average composition formula $CH_2=CH—Si(OSiMe_3)_3$ were placed in a reaction vessel, and 0.39 g of a hexamethyl disiloxane solution of platinum-1,3-divinyl-1,1,3,3-tetramethyl disiloxane complex (Pt concentration 0.4 wt. %) was added while stirring under a nitrogen flow at 25° C. The reaction liquid was heated to 65 to 75° C. and allowed to react for 4 hours. Then, 2 g of the reaction liquid was sampled and it was confirmed that the reaction rate was not in error through an alkali decomposition gas generation method.

Step 2: 47.3 g of hexadecene (α olefin purity=91.7%) was added to the reaction liquid (first adding) and the heat generated thereby caused the temperature to rise from 32° C. to 58° C. It was confirmed that the target reaction rate had been achieved by the same alkali decomposition gas generation method as in step 1.

Step 3: 23.1 g of the monoallyl diglycerin obtained in Working Example 2, 0.035 g of natural vitamin E, and 245.0 g of IPA were added to the reaction liquid, and then an additional 0.39 g of the same platinum catalyst solution as above was infused. When reacted for 4 hours at 45 to 65° C., it was confirmed that the target reaction rate had been achieved by the same method as in step 1.

Step 4: 50.7 g of hexadecene (second adding) and an additional 0.39 g of the same platinum catalyst solution as above were added to the reaction liquid and reacted for 6 hours at 60 to 70° C. The reaction was completed upon confirmation by the same method as in step 1.

Step 5: IPA was distilled out under reduced pressure at 70 to 80° C., and stripping was further started under conditions of 95 to 125° C. and 10 Torr. The system gradually thickened after starting, and the contents gelled after 20 minutes, making it impossible to stir.

Comparative Example 5: <Modified Silicone Synthesis>

265 g of a composition containing a diglycerin derivative-modified silicone represented by the average composition formula $MD_{47.5}D^{R*11}{}_{7.5}D^{R*31}{}_1D^{R*22}{}_2M$ was obtained in the same manner as in Working Example 6, except that an allyl diglycerin derivative (GC purity 31%) was used that had been obtained by causing a ring opening reaction of one mole of glycidol on one mole of glycerin monoallyl ether according the known glycidol polymerization method described, for example, in Japanese Unexamined Patent Application Publication No. 2004-277548A. The product was a uniform, opaque pale brown liquid.
In this formula, $R^{*11}=—C_{12}H_{25}$.
$R^{*31}=—C_2H_4Si(OSiMe_3)_3$
$R^{*22}$ is represented by —$C_3H_6O$—X, where "X" is the diglycerin portion.

Comparative Example 6: <Modified Silicone Synthesis>

137 g of a composition containing a diglycerin derivative-modified silicone represented by the average composition formula $MD_{47.5}D^{R*11}{}_{7.5}D^{R*31}{}_1D^{R*22}{}_2M$ was obtained in the same manner as in Working Example 7, except that an allyl diglycerin derivative (GC purity 31%) was used that had been obtained by causing a ring opening reaction of one mole of glycidol on one mole of glycerin monoallyl ether according the known glycidol polymerization method described, for example, in Japanese Unexamined Patent Application Publication No. 2004-277548A. The product was a uniform, opaque pale brown liquid.
In this formula, $R^{*11}=—C_{12}H_{25}$.
$R^{*31}=—C_2H_4Si(OSiMe_3)_3$
$R^{*22}$ is represented by —$C_3H_6O$—X, where "X" is the diglycerin portion.

Evaluation of Emulsification Performance

The water-in-oil emulsion compositions shown in Table 2 were prepared as described below, using silicone compounds obtained in Working Example 6, Comparative Example 3, and Comparative Example 5, and the emulsion particle size and stability of the prepared compositions were evaluated. The results are shown in Table 2. In the table, "parts" indicates "parts by weight (mass)".

[Preparation Method for Water-in-Oil Emulsion Composition]
1. A silicone compound comprising an oil agent and a surfactant was placed in a 200 mL container.
2. The compound was stirred and the surfactant was uniformly dispersed or dissolved in the oil agent (oil phase A).
3. Table salt and ion exchanged water were placed in a separate container. The salt was dissolved by mixing using a spatula. Furthermore, 1,3-butylene glycol was mixed and dissolved therein (aqueous phase B).
4. The saw teeth of the homogenizing disperser were immersed in the oil phase A and, the aqueous phase B was poured into the oil phase A at a constant rate over a period of about 45 seconds, while stirring at 1,000 rpm.
5. The rotational speed of the homogenizing disperser was increased to 3500 rpm, and the contents were homogeneously emulsified by stirring for 2 minutes.
6. Stirring was stopped. Then, the oily component adhered to the inner wall of the container was scraped off using a spatula and mixed with the produced emulsion.

7. The contents were homogeneously emulsified by stirring for 3 minutes with the rotational speed of the homogenizing disperser at 3500 rpm.

[Assessment of stability of emulsion composition] 28 g of each water-in-oil emulsion composition was measured into 35 ml glass bottles, sealed with stoppers, and left to sit for two months in a 50° C. thermostatic chamber. Changes in viscosity were measured after 2 weeks, after one month, and after two months, and stability was assessed by the extent of change in viscosity.

[Viscosity measurement] The viscosity of emulsion compositions was measured at 25° C. using a VISCOMIC EMD E-type viscometer manufactured by Tokyo Keiki, Inc.

[Emulsion particle size measurement] Emulsion compositions were observed (1000× magnification) and photographed with an optical microscope, and the weight-average particle size was computed using image analysis software.

It was thus shown that the purity of the raw material is related to the emulsion stability when used as an emulsifier for modified silicone.

[Particle dispersion performance assessment] Particle-in-oil dispersions of the compositions shown in Table 3 were prepared using the modified silicones obtained in Working Example 7 and Comparative Example 6, and the viscosity stability of the dispersion was assessed according to the following assessment criteria. The results are shown in Table 3. In the table, "parts" indicates "parts by weight (mass)".

Working Examples 11, 12 and Comparative Examples 13, 14

Particle-in-oil dispersion was prepared by mixing and dispersing the compositions shown in Table 3 according to

TABLE 2

| | | Working Example | | Comparative Example | | | | |
|---|---|---|---|---|---|---|---|---|
| | | 8 | 9 | 7 | 8 | 9 | 10 | 11 |
| Oil phase A | Emulsifier (Working Example 6) | 2.0 | 2.0 | 0 | 0 | 0 | 0 | 0 |
| | Emulsifier (Comparative Example 5) | 0 | 0 | 2.0 | 2.0 | 0 | 0 | 0 |
| | Emulsifier (Comparative Example 3) | 0 | 0 | 0 | 0 | 2.0 | 2.0 | 2.0 |
| | Dimethylpolysiloxane (6 cSt) | 11.5 | 0 | 11.5 | 0 | 23.0 | 11.5 | 0 |
| | Mineral oil 50SUS (37.8° C.) | 11.5 | 23.0 | 11.5 | 23.0 | 0 | 11.5 | 23.0 |
| Aqueous phase B | Ion exchange water | 68.5 | 68.5 | 68.5 | 68.5 | 68.5 | 68.5 | 68.5 |
| | 1,3-butylene glycol | 6.0 | 6.0 | 6.0 | 6.0 | 6.0 | 6.0 | 6.0 |
| | Table salt | 0.5 | 0.5 | 0.5 | 0.5 | 0.5 | 0.5 | 0.5 |
| | Total | 100.0 | 100.0 | 100.0 | 100.0 | 100.0 | 100.0 | 100.0 |
| | Emulsion composition average particle size (μm) | 3.2 | 3.5 | 3.9 | 3.8 | 3.5 | 3.7 | 3.3 |
| Emulsion composition viscosity (mPa·s) | Initial | 3100 | 3090 | 3130 | 3290 | 3940 | 3280 | 3300 |
| | After 2 weeks at 50° C. | 3090 | 3150 | 3210 | 3630 | 4010 | 3250 | 3490 |
| | After 1 month at 50° C. | 3200 | 3110 | 3400 | 3580 | Separated | 3430 | 3560 |
| | After 2 months at 50° C. | 3080 | 3160 | 3600 | 3630 | Separated | Separated | Separated |
| | Percent change in viscosity in 2 months | −1% | +2% | +15% | +10% | Separated | Separated | Separated |

* In the table, viscosity is the measured value obtained according to the viscosity measurement method described above at 10 rpm cone rotation.

The above results show that the diglycerin derivative-modified silicone of Working Example 6, synthesized using high-purity monoallyl diglycerin as raw materials, had stable viscosity, regardless of the oil agent used. On the other hand, when the diglycerin derivative-modified silicone of Comparative Example 3 or 5, synthesized using low-purity monoallyl diglycerin as raw materials, was used, a tendency was discovered for viscosity to increase over time, while phase separation observed in Comparative Examples 9 to 11.

the following procedure. Furthermore, the unit of all numeric values in the formulations shown in Table 3 below is grams (g).

(Preparation Procedure)

1. Decamethylcyclopentasiloxane (D5) and silicone compound (dispersion) were placed in a 200 ml glass bottle, stirred, and dissolved.

2. Particles and zirconia balls (YTZ balls, 0.8 mm diameter) with 10-times the mass of the particles were placed in the above glass bottle and thoroughly stirred at 3000 to 3500 rpm for 3 minutes with a homogenizing disperser. The following particles were used.
Titanium oxide: MTY-02 (manufactured by Tayca Corporation)
Zinc oxide: FINEX-30S-LP2 (manufactured by Sakai Chemical Industry Co.)
3. The glass bottle was set in a paint shaker and shaken for 15 minutes.
4. The resulting mixture was passed through a sieve to remove the zirconia balls, yielding a particle-in-water dispersion.

TABLE 3

|  | Working Example 11 | Comparative Example 13 | Working Example 12 | Comparative Example 14 |
|---|---|---|---|---|
| D5 | 15 | 15 | 10.5 | 10.5 |
| Modified silicone (Working Example 7) | 3 | — | 1.5 | — |
| Modified silicone (Comparative Example 6) | — | 3 | — | 1.5 |
| Titanium oxide | 12 | 12 | — | — |
| Zinc oxide | — | — | 18 | 18 |
| Viscosity (initial) | 188 | 264 | 288 | 392 |
| Viscosity (after 2 weeks) | 205 | 1164 | 140 | 691 |
| Viscosity (after 4 weeks) | 119 | 1016 | 124 | 869 |

* In the table, viscosity is the measured value obtained according to the viscosity measurement method described above at 10 rpm cone rotation.

The above results show that the diglycerin derivative-modified silicone of Working Example 7, synthesized using high-purity monoallyl diglycerin as raw material, had stable viscosity, regardless of the particles used. On the other hand, when the diglycerin derivative-modified silicone of Comparative Example 6, synthesized using low-purity monoallyl diglycerin as raw material, was used, a tendency was discovered for viscosity to increase over time, revealing a relationship between the purity of the raw material and slurry stability when modified silicone is used as a dispersant.

Hereinafter, formulation examples of the cosmetic composition and the external use preparation according to the present invention are described, but it is understood that the cosmetic composition and the external use preparation according to the present invention are not limited to the types and compositions recited in these formulation examples.

Glycerin derivative-modified silicone obtained by reacting the high-purity monoalkenyl-containing glycerin derivative of the present invention can be used in a variety of external use preparations and cosmetic compositions. Thus, substituting glycerin derivative-modified silicone obtained by reacting the high-purity monoalkenyl-containing glycerin derivative of the present invention, above, for the ingredients corresponding to silicone compound Nos. 1 to 16 in the example formulations for various cosmetic compositions and external use preparations disclosed in the working examples described by the Applicants in Patent Document 6, above, is encompassed within the scope of the present invention as example formulations of cosmetic compositions and external use preparations associated with the present invention.

Specifically, the following example formulations are disclosed in paragraphs 0459 to 0501 of Patent Document 6, above, in working examples of emulsion, lip gloss, oil foundation, water-in-oil emulsion transparent antiperspirant composition, and nonaqueous stick antiperspirant composition as compositions that can be substituted with glycerin derivative-modified silicone obtained by reacting the high-purity monoalkenyl-containing glycerin derivative of the present invention. Using compositions containing glycerin derivative-modified silicone obtained by reacting the high-purity monoalkenyl-containing glycerin derivative of the present invention in the example formulations improves the stability of each cosmetic formulation. In particular, because finely stable emulsion and dispersion can be obtained with formulations that comprise an emulsion or dispersion system, secondary effects, such as improved ultraviolet blocking effect and improved cosmetic durability, can be expected in makeup coloring and skin care. Furthermore, in addition to the essential effects of these formulations, substantial advantages are also produced in that the preparations produce virtually no odor over time, and that there is virtually no change in scent over time.

Example 1: Emulsion foundation
Example 2: Liquid foundation
Example 3: Foundation
Example 4: Water-in-oil cream
Example 5: Water-in-oil emulsion composition
Example 6: Water-in-oil emulsion rouge (liquid)
Example 7: Liquid rouge
Example 8: Rouge
Example 9: Sunscreen emulsion
Example 10: Emulsion
Example 11: UV blocking cream
Example 12: UV blocking water-in-oil emulsion
Example 13: Sunscreen agent
Example 14: Water-in-oil emulsion sunscreen
Example 15: O/W cream
Example 16: Eye shadow
Example 17: Mascara
Example 18: Mascara
Example 19: Solid powder eye shadow
Example 20: Pressed powder cosmetic
Example 21: Powder foundation
Example 22: Pressed foundation
Example 23: Cream
Example 24: Foundation
Example 25: Water-in-oil emulsion-type sunscreen
Example 26: Lipstick
Example 27: Rouge
Example 28: Foundation
Example 29: Antiperspirant aerosolized cosmetic composition
Example 30: Nonaqueous pressurized antiperspirant product
Example 31: Aerosol type antiperspirant composition
Example 32: Antiperspirant lotion composition
Example 33: W/O emulsion-type skin external use preparation
Example 34: Nonaqueous antiperspirant deodorant stick composition
Example 35: W/O solid antiperspirant stick composition
Example 36: W/O emulsion type antiperspirant cream composition
Example 37: Mascara
Example 38: Aftershave cream
Example 39: Solid foundation
Example 40: Daytime use skin-lightening cream
Example 41: Sun tanning cream
Example 42: Polyol/O-type nonaqueous emulsion skin external use preparation
Example 43: Polyol/O-type nonaqueous emulsion skin external use preparation Otherwise, substituting glycerin derivative-modified silicone obtained by reacting the high-purity monoalkenyl-containing glycerin derivative of the present invention (for example, Working Example 6) for the ingredients corresponding to silicone compound Nos. 1 to 14 in the example formulations for various cosmetic compositions and external use preparations disclosed in the working examples described by the Applicants in Patent Document 7, for example, is encompassed within the scope of the present invention as example formulations of cosmetic compositions and external use preparations associated with the present invention.

Specifically, the following example formulations are disclosed in paragraphs 0376 to 0400 of Patent Document 7, above, in working examples of lipstick, gel composition, emulsion cosmetic composition, and water-in-oil emulsion transparent soft gel antiperspirant as compositions that can be substituted with glycerin derivative-modified silicone obtained by reacting the high-purity monoalkenyl-containing glycerin derivative of the present invention. Using compositions that contain glycerin derivative-modified silicone obtained by reacting the high-purity monoalkenyl-containing glycerin derivative of the present invention produces substantial advantages in addition to the essential effects of these formulations in that the preparations produce virtually no odor over time, and that there is virtually no change in scent over time.

Example 1: Rouge
Example 2: Lipstick
Example 3: Rouge
Example 4: Rouge
Example 5: Oil-based solid eye shadow
Example 6: Eye liner
Example 7: Foundation
Example 8: Foundation
Example 9: Gel-like cosmetic composition
Example 10: Cream-like emulsion cosmetic composition
Example 11: Paste-like emulsion cosmetic composition
Example 12: Aerosol type antiperspirant composition
Example 13: Gel-like antiperspirant stick
Example 14: Oil-based gel type cleansing agent
Example 15: Gel-like antiperspirant stick
Example 16: Gel-like deodorant stick
Example 17: Gel-like cream
Example 18: Gel-like lip cream
Example 19: Mascara
Example 20: Gel-like aftershave cream
Example 21: Solid foundation
Example 22: Gel-like daytime use skin-lightening cream
Example 23: Polyol/O-type nonaqueous gel emulsion skin external use preparation
Example 24: Polyol/O-type nonaqueous gel emulsion skin external use preparation Otherwise, an ingredient corresponding to the low-odor glycerin derivative-modified silicone No. 1 in formulations mainly comprising the following hydrocarbon-based cosmetic bases disclosed in Patent Document 10 may be substituted with a glycerin derivative-modified silicone obtained by reacting the high-purity monoalkenyl-containing glycerin derivative of the present invention (for example, Working Example 6). Furthermore, PEG-free formulations can also be designed by replacing the entire amount of the polyether-modified silicone below with a glycerin derivative-modified silicone obtained by reacting the high-purity monoalkenyl-containing glycerin derivative of the present invention (for example, Working Example 6).

Formulation Example: Liquid Foundation (W/O)

Components
1. Isododecane 20 parts
2. Isohexadecane 10 parts
3. Isotridecyl isononanoate 3 parts
4. Glyceryl tricapryl-caprate 2 parts
5. Polyether-modified silicone[*1] 1.5 parts
6. Low-odor glycerin derivative-modified silicone No. 1 0.5 parts
7. Organo-modified clay mineral (Bentone 38V) 1.5 parts
8. Octyl methoxycinnamate 5 parts
9. Octylsilane treated titanium oxide 8.5 parts
10. Octylsilane-treated red iron oxide 0.4 parts
11. Octylsilane-treated yellow iron oxide 1 part
12. Octylsilane treated black iron oxide 0.1 parts
13. Dimethicone, dimethicone crosspolymer[*2] 2 parts
14. Isododecane/(acrylate/polytrimethylsiloxy methacrylate) copolymer[*3] 1 part
15. Trimethylsiloxysilicate 1 part
16. 1,3-Butylene glycol 5 parts
17. Glycerin 3 parts
18. Sodium chloride 0.5 parts
19. Preservative q.s.
20. Purified water Remainder
21. Perfume q.s.

[*1]: ES-5300, manufactured by Dow Corning Toray Co.
[*2]: DC9045, manufactured by Dow Corning
[*3]: FA-4002ID, manufactured by Dow Corning Toray Co.

Manufacturing Method
Step 1: Components 1, 2, 5, 6, 7, 8, 13, 14, and 15 are stirred and mixed.
Step 2: Components 3, 4, and 9 to 12 are kneaded and mixed using a three-roll mill.
Step 3: While stirring, add the compound of step 2 to the compound obtained in step 1 and stir/mix further.
Step 4: Add an aqueous phase formed by uniformly dissolving components 16 to 21 to the mixture obtained in step 3, emulsify, and fill a container with the emulsion. Thus, a product is obtained.

The obtained W/O type liquid foundation has no unpleasant odor, has excellent emulsion stability when used, has excellent moisture resistance and cosmetic durability, has excellent texture, masks wrinkles, has a light feeling to touch and has excellent adhesion.

The following can also be listed as example formulations of the cosmetic composition and external use preparation associated with the present invention.

Formulation Example: W/O Emulsion-Type Sunscreen Emulsion (Component) (wt. %)
1. D5 (decamethylcyclopentasiloxane) 26.6
2. Caprylyl methicone[*4] 5.0
3. BY 11-018[*5] 5.0
4. Octyldecyl myristate 10.0
5. Castor oil hydrogenated triisostearic acid PEG-20 0.3
6. Polyether-modified silicone[*6] 1.2
7. Glycerin derivative-modified silicone of the present invention (Working Example 7) 0.8
8. Disteardimonium hectorite 0.3
9. Dimethicone/methicone polymer-treated zinc oxide 15.0
10. Aluminum stearate-treated titanium oxide 13.0

11. Methylparaben 0.1
12. 95% ethanol 5.0
13. Magnesium sulfate 0.7
14. Perfume q.s.
15. Purified water 17.0

*4: FZ-3196, manufactured by Dow Corning Toray Co.
*5: D5 dilution containing 30% trimethylsiloxy silicic acid, manufactured by Dow Corning Toray Co.
*6: ES-5300, manufactured by Dow Corning Toray Co.

Manufacturing Method
A: Thoroughly blend components 1 to 11 to make a uniform dispersion.
B: Blend components 12 to 15 to make a uniform solution.
C: Add B to A and emulsify.

Effects
The sunscreen emulsion is substantially free of stickiness, and spreads very easily. Additionally, while having superior adhesive sensation, a discomfort free natural feeling on the skin is obtained. The emulsion has excellent stability, with minimal change in viscosity, such as increased viscosity, relative to either temperature or time. Usability is excellent.

Formulation Example: Bilayered (Shake Before Use to Mix Type) Sun Cut Lotion (Component) (wt. %)
1. D5 (decamethylcyclopentasiloxane) 23.6
2. Caprylyl methicone*4 7.5
3. DC 670Fluid*7 5.0
4. Liquid paraffin 3.0
5. Ethylhexyl methoxycinnamate 7.5
6. Polyether-modified silicone*6 1.0
7. Glycerin derivative-modified silicone of the present invention (Working Example 6) 1.0
8. Organic modified bentonite (Benton 38) 0.2
9. Methyl hydrogen polysiloxane-treated zinc oxide 22.5
10. 95% ethanol 5.0
11. 1,3-butylene glycol 3.0
12. Sodium citrate 0.2
13. Sodium chloride 0.5
14. Perfume q.s.
15. Purified water 20.0

*4 FZ-3196, manufactured by Dow Corning Toray Co.
*6 ES-5300, manufactured by Dow Corning Toray Co.
*7 D5 dilution containing 50% polypropyl silsesquioxane, manufactured by Dow Corning Corp.

Manufacturing Method
A: Thoroughly blend components 1 to 9 to make a uniform dispersion.
B: Blend components 10 to 15 to make a uniform solution.
C: Add B to A and emulsify.

Effects
Has the refreshing feel of water, spreads very lightly and well. Additionally, because the zinc oxide microparticles can be stably microdispersed due to the excellent particle dispersing effect of the product of the present invention, there is the advantage of not being likely to leave a white residue on the skin after application. Furthermore, there is no discomfort, such as a tense feeling, and ultraviolet protection effect is excellent.

Formulation Example: W/O Emulsion-Type Sun Cut Cream (Component) (wt. %)
1. EL-8040 ID*8 5.0
2. MQ-1640 Flake Resin*9 1.0
3. Glycerin derivative-modified silicone of the present invention (Working Example 6) 1.0
4. Isotridecyl isononanate 2.0
5. Isohexadecane 1.7
6. Powder-in-oil dispersion of Working Example 11 22.5
7. Powder-in-oil dispersion of Working Example 12 31.5
8. 1,3-butylene glycol 2.0
9. Sodium chloride 0.5
10. Purified water 32.8

*8 Isododecane dilution containing 16% dimethicone cross-polymer, manufactured by Dow Corning Corp.
*9 Blend of trimethylsiloxysilicic acid and polypropyl silsesquioxane, manufactured by Dow Corning Corp.

Manufacturing Method
A: After blending components 2 to 5 to make a uniform solution, add component 1 and blend thoroughly to make a uniform dispersion.
B: Blend components 8 to 10 to make a uniform solution.
C: After adding B to A and emulsifying, add components 6 and 7 and blend to yield an uniform cream.

Effects
Yields a unique, velvety, thick, and smooth application feel. Excellent ultraviolet protection effect and antiperspirant effect, with a fresh feel during use that is not sticky or greasy.

The invention claimed is:

1. A monoalkenyl-containing glycerin derivative with purity of not less than 92% and electrical conductivity of not greater than 50 μS/cm in 2.0 mass % aqueous solution at room temperature, wherein the monoalkenyl-containing glycerin derivative is a monoalkenyl-containing diglycerin.

2. A method of manufacturing a monoalkenyl-containing glycerin derivative with purity of not less than 92% and electrical conductivity of not greater than 50 μS/cm in 2.0 mass % aqueous solution at room temperature, the method comprising the following steps (A) through (C):
step (A): a step of reacting a ketalized glycerin derivative and a monoalkenyl glycidyl ether in the presence of an inorganic base to obtain a ketal of monoalkenyl-containing glycerin derivative;
step (B): a step of purifying the ketal of monoalkenyl-containing glycerin derivative obtained in the step (A) by distillation; and
step (C): a step of hydrolyzing the ketal of monoalkenyl-containing glycerin derivative obtained in the step (B) in the presence of an acid and an acidic inorganic salt.

3. The manufacturing method according to claim 2, wherein the inorganic base is selected from the group consisting of alkali metal hydroxides, alkali earth metal hydroxides, alkoxides of alkali metals, alkoxides of alkali earth metals, and mixtures thereof.

4. The manufacturing method according to claim 2, wherein the acid in the step (C) is hydrochloric acid or trifluoroacetic acid.

5. The manufacturing method according to claim 2, the method further comprising:
a step (D) of removing the acid or acidic inorganic salt after the step (C).

6. The manufacturing method according to claim 5, wherein the step (D) includes stripping.

7. The manufacturing method according to claim 6, wherein the step (D) includes reduced pressure stripping.

* * * * *